United States Patent
Ezumi et al.

(10) Patent No.: US 6,946,656 B2
(45) Date of Patent: Sep. 20, 2005

(54) SAMPLE ELECTRIFICATION MEASUREMENT METHOD AND CHARGED PARTICLE BEAM APPARATUS

(75) Inventors: Makoto Ezumi, Mito (JP); Yoichi Ose, Mito (JP); Akira Ikegami, Mito (JP); Hideo Todokoro, Hinode (JP); Tatsuaki Ishijima, Hitachinaka (JP); Takahiro Sato, Hitachinaka (JP); Ritsuo Fukaya, Hitachinaka (JP); Kazunari Asao, Hitachinaka (JP)

(73) Assignee: Hitachi, Ltd. (JP)

( * ) Notice: Subject to any disclaimer, the term of this patent is extended or adjusted under 35 U.S.C. 154(b) by 32 days.

(21) Appl. No.: 10/483,596

(22) PCT Filed: Jul. 10, 2002

(86) PCT No.: PCT/JP02/06994

§ 371 (c)(1),
(2), (4) Date: Feb. 10, 2004

(87) PCT Pub. No.: WO03/007330

PCT Pub. Date: Jan. 23, 2003

(65) Prior Publication Data

US 2004/0211899 A1 Oct. 28, 2004

(30) Foreign Application Priority Data

Jul. 12, 2001 (JP) ........................................ 2001-211532
Aug. 31, 2001 (JP) ........................................ 2001-262641

(51) Int. Cl.$^7$ ............................................... H01J 37/26
(52) U.S. Cl. ........................ 250/310; 250/306; 73/105; 324/662; 324/60 R
(58) Field of Search ................................ 250/310, 306; 73/105; 324/662, 60 R

(56) References Cited

U.S. PATENT DOCUMENTS

| | | | |
|---|---|---|---|
| 5,512,747 A | 4/1996 | Maeda | |
| 5,723,981 A | * 3/1998 | Hellemans et al. | ......... 324/719 |
| 5,872,358 A | 2/1999 | Todokoro et al. | |
| 6,635,873 B1 | 10/2003 | Todokoro et al. | |

FOREIGN PATENT DOCUMENTS

| | | |
|---|---|---|
| JP | 4-181643 | 6/1992 |
| JP | 5-67667 | 3/1993 |
| JP | 5-151927 | 6/1993 |
| JP | 7-176285 | 7/1995 |
| JP | 9-145764 | 6/1997 |
| JP | 9-171791 | 6/1997 |
| JP | 11-126573 | 5/1999 |
| JP | 2000-200579 | 7/2000 |
| JP | 2001-52642 | 2/2001 |

* cited by examiner

*Primary Examiner*—Nikita Wells
*Assistant Examiner*—Zia R. Hashmi
(74) *Attorney, Agent, or Firm*—Dickstein Shapiro Morin Oshinsky LLP

(57) ABSTRACT

The present invention has the object of providing a charged particle beam irradiation method ideal for reducing the focus offset, magnification fluctuation and measurement length error in charged particle beam devices.

To achieve these objects, a method is disclosed in the invention for measuring the electrical potential distribution on the sample with a static electrometer while loaded by a loader mechanism. Another method is disclosed for measuring the local electrical charge at specified points on the sample, and isolating and measuring the wide area electrostatic charge quantity from those local electrostatic charges. Yet another method is disclosed for correcting the measurement length value or magnification based on fluctuations found by measuring the amount of electrostatic charge at the specified points under at least two charged particle optical conditions, and then using a charged particle beam to measure fluctuations in measurement dimensions occurring due to fluctuations in the electrostatic charge at the specified locations.

32 Claims, 23 Drawing Sheets

Voltage distribution caused by characteristic electrostatic charge on wafer

Voltage distribution caused by beam irradiation

Overlapped voltage distribution

Predose magnification Mpre: when from small to large

Predose magnification Mpre: when from large to small

SAMPLE ELECTRIFICATION MEASUREMENT METHOD AND CHARGED PARTICLE BEAM APPARATUS

TECHNICAL FIELD

The present invention relates to a charged particle beam device and relates in particular to a measurement method and device thereof for inspecting or measuring the dimensions and shape of a pattern formed on a sample piece.

BACKGROUND ART

The greater scale of integration and miniaturization of semiconductor devices in recent years has resulted in many diverse patterns being formed on the wafer and makes it ever more important to evaluate and measure the dimensions and shapes of these patterns. How fast these measurement points can be detected is critical for quickly and automatically testing the numerous measurement points. During fast detection of measurement points, it is necessary to focus on the pattern after shifting to the measurement point and to also set the desired magnification (scale) for observing that point.

In charged particle optical systems, the conditions for focusing on the wafer are determined by the acceleration voltage of the charged particle supply, the voltage applied to the wafer, and the height of the wafer.

In the method disclosed for example in JP-A No. 126573/1999, a laser beam is irradiated onto the wafer, the height of the wafer is detected by using that reflected light, and the height information obtained in this way is fed back to an objective lens control system serving as one control device for the charged particle optical system, and the necessary excitation voltage is applied to the objective lens at the same time that movement to the observation point ends.

DISCLOSURE OF THE INVENTION

In recent years however, more and more wafers are being found to contain a static electrical charge or electrostatic charge that still remains even when the wafers are electrically grounded. The cause of this static or electrostatic charge may for example be due to a fixed electrical potential from splitting (split polarization) of polarized material within the resist due to friction during applying of the resist coating by a spin coater. Another possible cause is residual electrical charges from etching that uses plasma.

These residual electrostatic charges remaining on the sample can cause the focus of the charged particle beam to deviate and are a cause of magnification fluctuations and measurement errors in the charged particle beam device. A method is disclosed for example in JP-A No. 176285/1995 for resolving the focus deviation problem by storing a focus offset value for each measurement point on a scanning electron microscope to prevent focus deviations from interfering with automatic measurement. Another method is disclosed in JP-A No. 52642/2001 for installing electrometers at multiple points in proximity to the sample inside a vacuum and feeding a retarding voltage back as a value based on those measurement results.

However, the technology disclosed in JP-A No. 176285/1995 has the following problems. The electrostatic voltage on the wafer is determined by the temperature and humidity, state of the resist and plasma intensity in that manufacturing process, so the electrostatic voltage is not a fixed value even on wafers undergoing the same manufacturing process. So even if the focus deviation is stored in a file for making automatic measurements, the focus deviation has to be updated (rewritten) for each wafer. A long time is therefore needed to measure a wafer and this delay caused productivity to drop. The electrostatic electrical potential also still remained unchanged on the wafer so that the actual accelerating voltage is different from the accelerating voltage actually needed. This differential causes differences in contrast and tiny structures to appear in secondary charged particle phenomenon that are formed. Other problems also still unresolved included errors in controlling the magnification, etc.

In the method disclosed in JP-A No. 52642/2001, using electrometers installed within a vacuum, the electrostatic electrical potential cannot be measured without moving to the measurement point so a long time was required to make a measurement at one point. Another problem is that when a breakdown occurred, the charged particle and stage in the vacuum unit has to be exposed to the outside air so that maintenance of the equipment is difficult. Yet another problem is that the multiple electrometers have to be adjusted to constantly provide the same output.

A first object of the present invention is to provide a device and method for detecting the characteristic electrostatic charge state of the sample without having to also measure the electrostatic charge at each measurement point.

A second object of the present invention is to provide a method ideal for reducing or eliminating measurement errors or fluctuations in magnification due to electrostatic charges, a magnification adjustment method, and a device to implement these methods.

To achieve the first object, a technique is proposed in the present invention for measuring the electrical potential distribution on the sample by utilizing a static electrometer to measure the voltage on the sample during movement of the sample being loaded by the loader of the charged particle beam device.

To achieve the second object, a technique is proposed in the present invention for measuring electrostatic charges at specified points on the sample, and from that electrostatic charge quantity then isolating and measuring the wide area electrostatic charge. As another method to achieve the second object, the electrostatic charge quantity at specified locations is irradiated under at least two charged particle irradiation conditions, and a fitting coefficient is formed that expresses changes in the electrostatic charge voltage from changes in the irradiation conditions, and the pattern dimensions are then corrected based on the feedback coefficient thus formed.

The best modes for carrying out the invention are described next in detail using the specific embodiments of the present invention.

Figure 1:
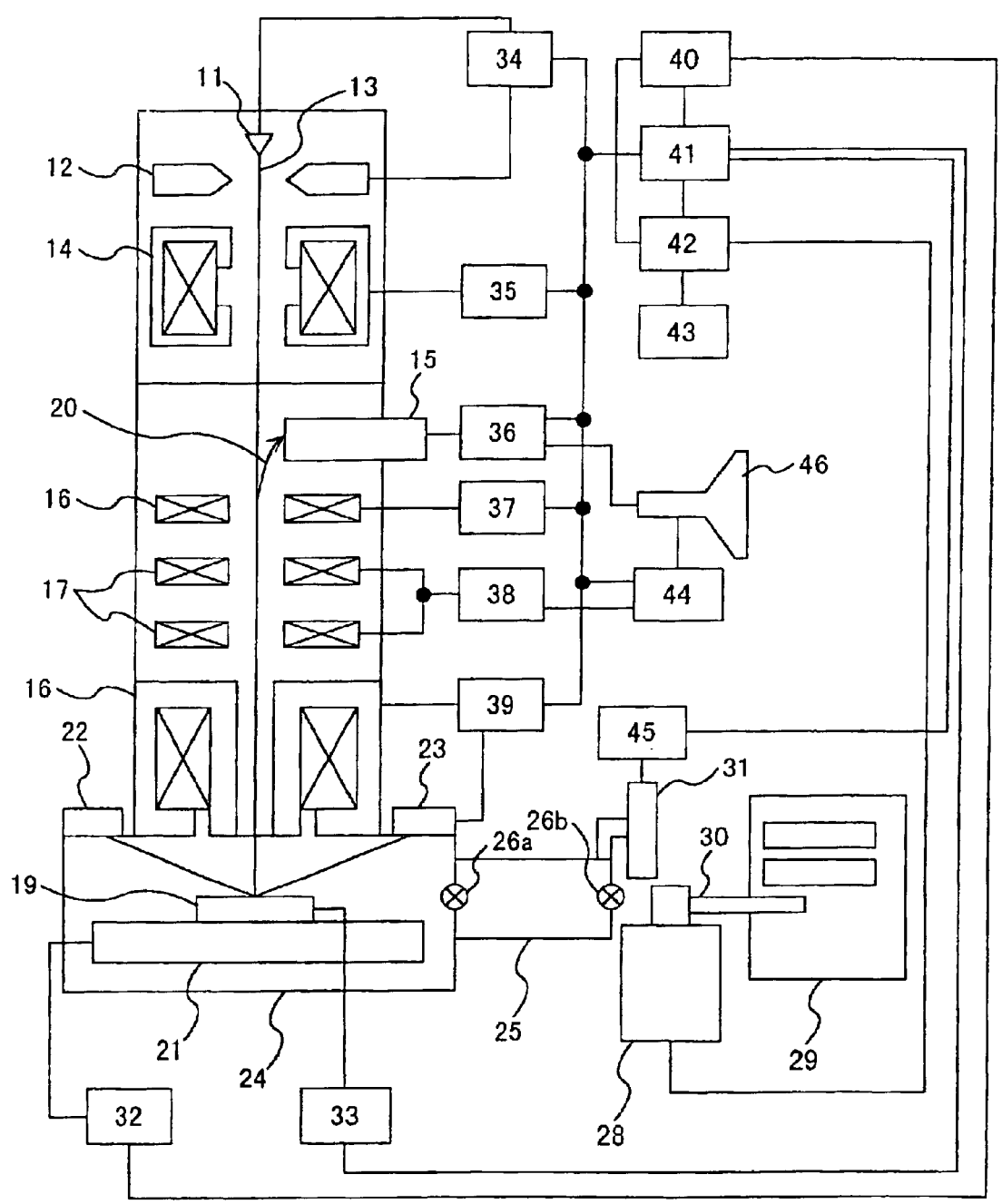
FIG. 1 is a diagram showing the overall structure of the scanning electron microscope.

BEST MODE FOR CARRYING OUT THE INVENTION (First Embodiment)

The embodiments of the present invention are described next while referring to the drawings. The example in the embodiment was described as using a scanning electron microscope (SEM). However, the present invention is not limited to this and other charged particle beam devices such as ion beam irradiation devices can be used. The example in the present embodiment also describes detecting secondary electrons and/or reflected electrons which are one type of charged particle. However, the present invention is not limited to this and may detect other charged particles such as secondary ions, etc.

FIG. 1 shows the overall structure of the present invention. An integrated controller 42 controls the overall device via the charged particle optical system controller 41, stage controller 40, and wafer conveyor 28, based on the observation position information, wafer information and acceleration voltage of the charged particle entered by the operator from the user interface 43.

The wafer conveyor 28 extracts the wafer from the wafer cassette 29 using the conveyor arm 30 after receiving an instruction from the integrated controller 42. The wafer conveyor 28 opens the gate valve 26b separating the sample exchange chamber 25 maintained in a vacuum from an external section connecting to the outer atmosphere. The wafer conveyor 28 loads the wafer into the sample exchange chamber. The wafer inserted in the sample exchange chamber is conveyed to a sample chamber 24 via the gate valve 26a and is clamped onto the sample stage 21.

The charged particle optical system controller 41 controls a high voltage controller 34, a retarding controller 33, a condenser lens controller 35, an amplifier 36, an alignment controller 37, a deflection signal controller 44, and an objective lens controller 39 according to instructions received from the integrated controller 42. A primary charged particle beam 13 pulled from the charged particle supply 11 by the pull-up electrode 12 is irradiated onto the wafer 19 after being focused by the condenser lens 14 and objective lens 18. During the above process, the path of the charged particle beam is aligned by the alignment coil 16. The upper part of the wafer is also scanned two-dimensionally by a signal received by the deflecting coil 17 from a deflecting signal controller via a deflecting signal amplifier 38. In the following description, a signal for changing the optical conditions of the charged particle beam is sent to each optical element and calculated in a section called a controller, control device or control processor, etc.

A retarding voltage (negative voltage when using an electron microscope) is applied to the wafer from the retarding controller 33 to decelerate the charged particle beam. The irradiating of the primary charged particle beam 13 onto the wafer 19 causes secondary charged electrons 20 to be emitted from the wafer. These secondary electrons 20 are then trapped by the secondary charged electron detector 15 and are used via an amplifier as luminance signals for the secondary charged electron display device 46. The secondary charged electron display device deflection signal is synchronized with the deflection signal from the deflection coil so the pattern shape of the wafer is faithfully reproduced on the secondary charged electron display device.

In order to test and observe the pattern on the wafer at high speed, a sample stage detects the wafer height when the wafer has moved to the desired observation point. The focus of the objective lens must then be aligned according to that height. A function is therefore installed in order to detect that wafer height by using light. The sample stage position detector 32 detects the position of the sample stage. At the point where the sample stage is close to the desired position, a height detection laser emitter 22 irradiates light towards the wafer. This reflected light is received by the position sensor 23 and the wafer height detected from that received light position. The amount of focus determined according to this detected height is then fed back to the objective lens. The focus is therefore already set when the sample stage arrived at the specified position and the pattern can be automatically detected without the intervention of the operator.

If there is no electrostatic charge on the wafer, the excitation current required for focusing the objective lens is generally expressed by the following function (1).

$$I_{obj} = F(V_o, V_r, Z) \qquad (1)$$

Here, $I_{obj}$ is the excitation current for the objective lens when there is no electrostatic charge on the wafer, F is the function for calculating the excitation current of the objective lens, $V_o$ is the voltage of the charged particle supply, $V_r$ is the wafer electrical potential, (retarding voltage applied to the wafer), Z is the height of the wafer. The function F can be derived by electron optical simulation or by actual measurement. A fixed focus control can be used to establish a relation shown in formula (1) for applying a retarding voltage with a electrical potential equivalent to a wafer usually having no electrostatic charge. However, when the wafer itself contains an electrostatic charge then the excitation current value required by the objective lens is as shown in formula (2). The focus current will differ depending on whether the wafer holds or does not hold an electrostatic charge.

$$I_{obj}' = F(V_o, V_g', Z) \quad (2)$$

Therefore, due to this difference the focus cannot be aligned no matter how accurately the height is detected, so the secondary charged particle image will appear blurred, detection at the observation point will fail and automatic measurement will be impossible. Here $I_{obj}'$ is the excitation current of the objective lens when the wafer holds an electrostatic charge, $V_g'$ is the total voltage of the retarding voltage $V_r$ and the wafer electrostatic voltage $\Delta V_g$ or in other words, $V_g = V_r + \Delta V_g$.

The electrostatic charge on the wafers differs according to factors such as the resist and the material in the underlayer but in most cases is in a concentric circular shape. The present invention measures the amount of electrostatic charge in this concentric circular shape on the wafer and then uses this electrical potential as feedback. The wafer stored inside the wafer cassette is extracted by the conveyor arm 30 (conveyor mechanism) and is measured by the probe 31 while being conveyed in the sample exchange chamber. The measured value is reported to the charged particle optical system device via the static electrometer 45.

In the example described in the present embodiment, the probe for measuring the electrical potential on the sample is above the movement path of the sample being conveyed by the conveyor mechanism and installed at a position separated from the material. However the present invention is not limited to this example. The probe for example may be installed on the movement path of the device for delivering and accepting the sample in the preheat chamber from the sample chamber, or the device for conveying the sample into the preheat chamber from the outside.

In the above example, the wafers tended to have an electrostatic charge in a concentric circular shape. So the overall electrical potential across the entire sample can be found by measuring the electrical potential distribution in a linear shape including the center position on the wafer surface. The following description shows an example particularly effective for measuring this kind of electrical potential distribution with a scanning electron microscope on a sample such as a semiconductor wafer.

Figure 2:
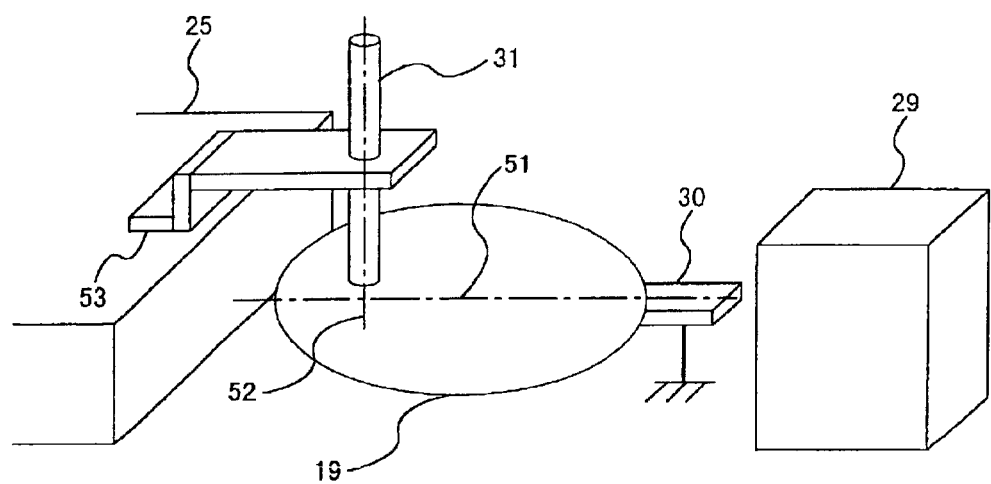
FIG. 2 is a drawing showing the relative positions of the wafer, conveyor arm, and static electrometer on the conveyor path.

FIG. 2 is a drawing showing the relative positions of the wafer cassette, and the conveyor arm as an essential element of the sample loader device, and the wafer, and static electrometer and sample exchange chamber. The wafer is extracted by the conveyor arm 30 from the wafer cassette 29 and conveyed into the sample exchange chamber 25. The probe 31 of the static electrometer is clamped onto the clamp bed 53 above the conveyor path of the wafer and further so that the center line 52 aligns with the wafer center line 51 above the wafer. The static electrometer probe measures the voltage of both the wafer and the grounded conveyor arm so that a more accurate value can be obtained by calibrating the wafer electrical potential based on the ground potential of the conveyor arm. The position the wafer will pass is a permanently fixed position, and since the probe is also clamped to the clamp bed, the relation of these two positions will not change so stable measurements can always be made. The probe is outside of the vacuum so even if the probe becomes defective, it can easily be repaired or replaced.

In the present embodiment, the probe was installed outside the vacuum to make handling easier. However, the invention is not limited to this and the probe may be installed anywhere along the path of the wafer. Also in this embodiment, the wafer is moved so that the center of the probe is aligned with the center line of the wafer. However the present invention is not limited to this example. As described above, the electrostatic charge on the wafer is a concentric circular shape in most cases. When the distribution of this electrostatic charge takes the form of a so-called peak, where the wafer center is the highest point and the electrostatic charge becomes lower towards the edge of the wafer, even if the probe center is somewhat offset from the centerline of the wafer, the overall electrical potential distribution can be determined. The overall electrical potential distribution can therefore also be determined from a linear shaped electrical potential distribution that is offset from the wafer center.

Figure 3:
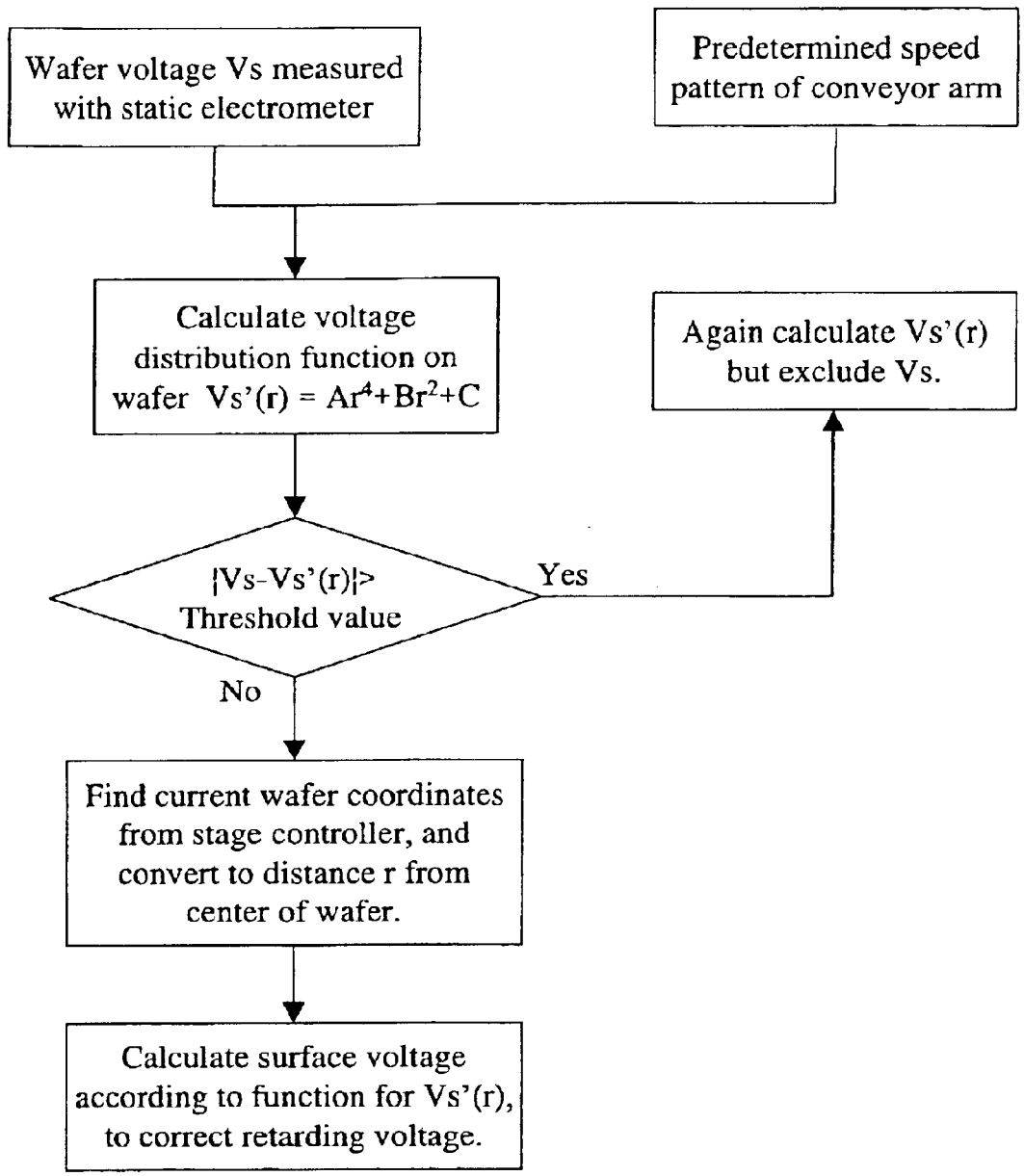
FIG. 3 is a diagram showing the flow of the method for determining the electrostatic charge distribution coefficient on the wafer surface.

FIG. 3 is a chart expressing the electrostatic charge voltage measured from the surface electrical potential as a distribution coefficient above the wafer surface. FIG. 3 also shows the retarding feedback procedure. The conveyor arm for the wafer does not usually operate at a constant speed so even if the measurement time is a fixed period time-wise, the coordinates on the wafer will not be at fixed intervals from each other. However an electrical potential corresponding to accurate coordinates can be obtained if the coordinates on the wafer are calculated from the speed pattern of the conveyor arm during the electrical potential measurement. A distribution function for the electrical potential can be made based on this acquired data. An approximate expression is first created as an even function (quartic function in FIG. 3) based on all of this acquired data.

Next, the differential at each measurement point versus this approximate expression is calculated. The electrical potential measurement value contains an error. When this differential (value) is larger than an established threshold, it is excluded since the error in the measurement is large. An approximate expression is once again formed without the excluded data. This process is repeated several times and ends when the differential for all values is smaller than the threshold. The function made in this way is a function expressing the distance from the center of the wafer as the electrical potential.

The electrical potential for making the correction is calculated from this function, and from the stage coordinates acquired from the stage controller device. This correction voltage is supplied to the wafer via the retarding controller shown in FIG. 1. Data is acquired each time the wafer under observation is conveyed to the sample exchange chamber. This data is valid until wafer observation ends and an instruction to return the wafer to the original wafer cassette is issued.

The embodiment of the present invention was described above. In the embodiment of the invention, a method was described for feeding back the measured electrostatic charge of the wafer unchanged, as retarding voltage. However, the electrostatic charge voltage made be converted to an excitation current for the objective lens and fed back. In that case however, the retarding voltage and the wafer electrostatic charge voltage added together should not exceed the voltage of the charged particle power supply. If the voltage of the charged particle power supply for example is −2000 volts, then when the charged particle voltage needed for beaming onto the sample is −300 volts, the retarding voltage applied to the wafer must be −1700 volts.

Under these conditions, consider the case when observing a wafer having a maximum electrostatic charge of −290 volts. Here, the primary charged particle beam can still reach the sample even if a voltage is applied as a retarding voltage to correct the −290 volt static charge, or even if that voltage is converted to an excitation current and applied to the objective lens. However, on a wafer with a maximum electrostatic charge of −310 volts, the combined retarding voltage and electrostatic voltage will total −2010 volts thus exceeding the charged particle power supply voltage.

In that case, the primary charged particle beam will not be able to reach the sample and is reflected away. A voltage of 310 volts must be applied as a retarding voltage to compensate for the −310 volts. The measured voltage may also be fed back to the charged particle power supply instead of applying it as a retarding voltage. Also in the embodiment of the present invention, instead of using a magnetic field lens whose high inductance makes high speed control difficult as the feedback destination for the retarding voltage, an electrostatic lens may be installed as the objective lens, or an electrostatic lens separately installed along with a magnetic field lens. A focus correction value based on the electrostatic charge voltage can then be fed back to these static lenses.

Among other methods for aligning the focus, when the SEM employs the so-called boosting method wherein a positive voltage is applied to tubular electrodes inside the objective lens, the focus can be aligned by adjusting this positive voltage. Most other technology for aligning the focus of the electron beam may also be utilized.

Figure 4:
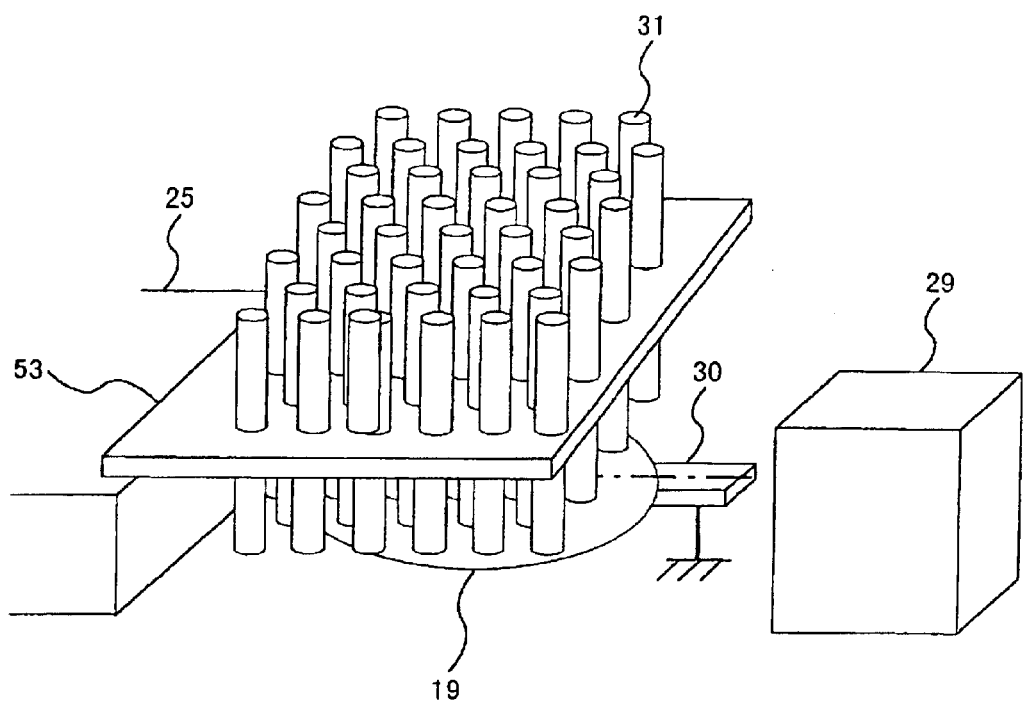
FIG. 4 is a drawing showing the method for measuring the electrostatic voltage on the wafer with multiple probes.

In the present invention, one static electrometer probe is installed to align with the center of the wafer; however, multiple probes may also be installed. FIG. 4 is a drawing of a structure for measuring the entire wafer surface with multiple probes arrayed along the wafer conveyance path. Here, multiple probes 31 are arrayed in a matrix on the clamp bed. In this case, the wafer 19 is temporarily stopped at a specified position along the conveyance path and the electrostatic charge measured at the respective points. This method has the advantages that there is no need to worry about the relation between speed or coordinates since the conveyor arm has stopped. Another advantage is that a distribution coefficient can be obtained even when the electrostatic charge does not have a symmetrical distribution. Also, the measuring points have already been established so that during fully automatic inspection of the semiconductor pattern width or fault inspection with the scanning electron microscope, those measurement points or the electrostatic charge near those points can be selectively tested and feedback then applied.

The present embodiment need not only use just feedback based on the quantity of electrostatic voltage, but may also combine it with other information to find a feedback value for the retarding voltage. Further, when a problem has occurred in the static electrometer due to any number of causes, and feedback is applied to the retarding voltage, conversely the focus value itself might then deviate. In such cases another means may be installed to evaluate the focus. When a problem then appears in the focus evaluation value, then a means may also be installed to perform fault diagnosis of the static electrometer, stop the focus feedback process based on the electrostatic charge measurement, and warn the operator of the abnormality.

As explained above, the present invention is capable of correcting the electrostatic charge even on wafers where focus offsets have occurred due to electrostatic charges and the success (pass) rate for pattern detection during automatic measurement has dropped. The present invention is also capable of automatically measuring wafers in the same way as wafers with no electrostatic charge. The invention further has the merit that the electrostatic charge voltage can be measured on each wafer so that measurement files are not needed and also that the file does not have to be revised according to whether or not there is an electrostatic charge or the size of that charge.

(Second Embodiment)

In view of the problems in making accurate tests and measurements in particular when different electrostatic charge phenomenon occur in the sample (semiconductor wafer, etc.), the embodiment described next relates to a device and method allowing highly precise testing and measurement even when different electrostatic charge phenomenon.

In a charged particle beam device, output information from a secondary charged particle detector is synchronized with the scanning by the charged particle beam and reproduced on an image display device as described above. The ratio of distance A between two points on the scanned image on the CRT (or display device) versus the distance a between two points on the sample, is the observation magnification $M_{SEM}$.

$$M_{SEM}=A/a$$

The distance a between two points on the sample is usually in inverse proportion to the observation magnification $M_{SEM}$ since the screen on the display device is a fixed size. By therefore measuring the distance A between the two points on the scanned image on the display, and dividing A by the observation magnification $M_{SEM}$, we can derive the line dimension as $a=A/M_{SEM}$.

Along with the advances in miniaturization in the semiconductor industry in recent years, the SEM is being used in place of the optical microscope in semiconductor fabrication processes or in testing after the fabrication process (for example, electrical operation tests or dimension measurements using the electron beam). In the sample (wafer) used by the semiconductor industry as the insulation, fluctuations in the insulation are occurring over time due to irradiation by the primary electron beam and causing deterioration in the scanned image.

A typical technology to resolve this problem was disclosed in JP-A No. 151927/1993 constituting a predose method wherein the SEM emitted (irradiated) a primary electron beam at a magnification different from the magnification during observation, and a static charge was progressively generated on the surface of the sample. A retarding method and a boosting method were next developed as disclosed in JP-A No. 171791/1997. In these methods, the retarding voltage applied to the sample was adjusted, and by observation with a primary electron beam having a low acceleration voltage below one kilovolt, a positive static charge was formed on the insulation. These methods generated a stable surface static charge for recreating the image and further attained a high resolution of approximately 3 nanometers.

Following this, a method was developed utilizing a SEM as in JP-A No. 200579/2000 wherein instead of a primary electron beam during the usual observation, an energy electron beam was first irradiated (onto the sample) to progressively generate a surface electrostatic charge. These methods allowed easily generating a stable, high surface electrostatic voltage and permitted observations of electrical potential contrast based on the difference in electrostatic charge voltage and the film remaining on the bottom of contact holes with a high aspect ratio.

However, when observing under the condition of this surface electrostatic charge voltage, it was found that a fluctuation of some several percent occurred in the measurement dimension values as the surface electrostatic charge was increased. Due to ever shrinking sizes in the semiconductor process, these fluctuations in measurement dimensions exceeded their allowable thresholds. The cause of the problem was fluctuations in observation magnification $M_{SEM}$ accompanying the surface electrostatic charge.

Figure 9:
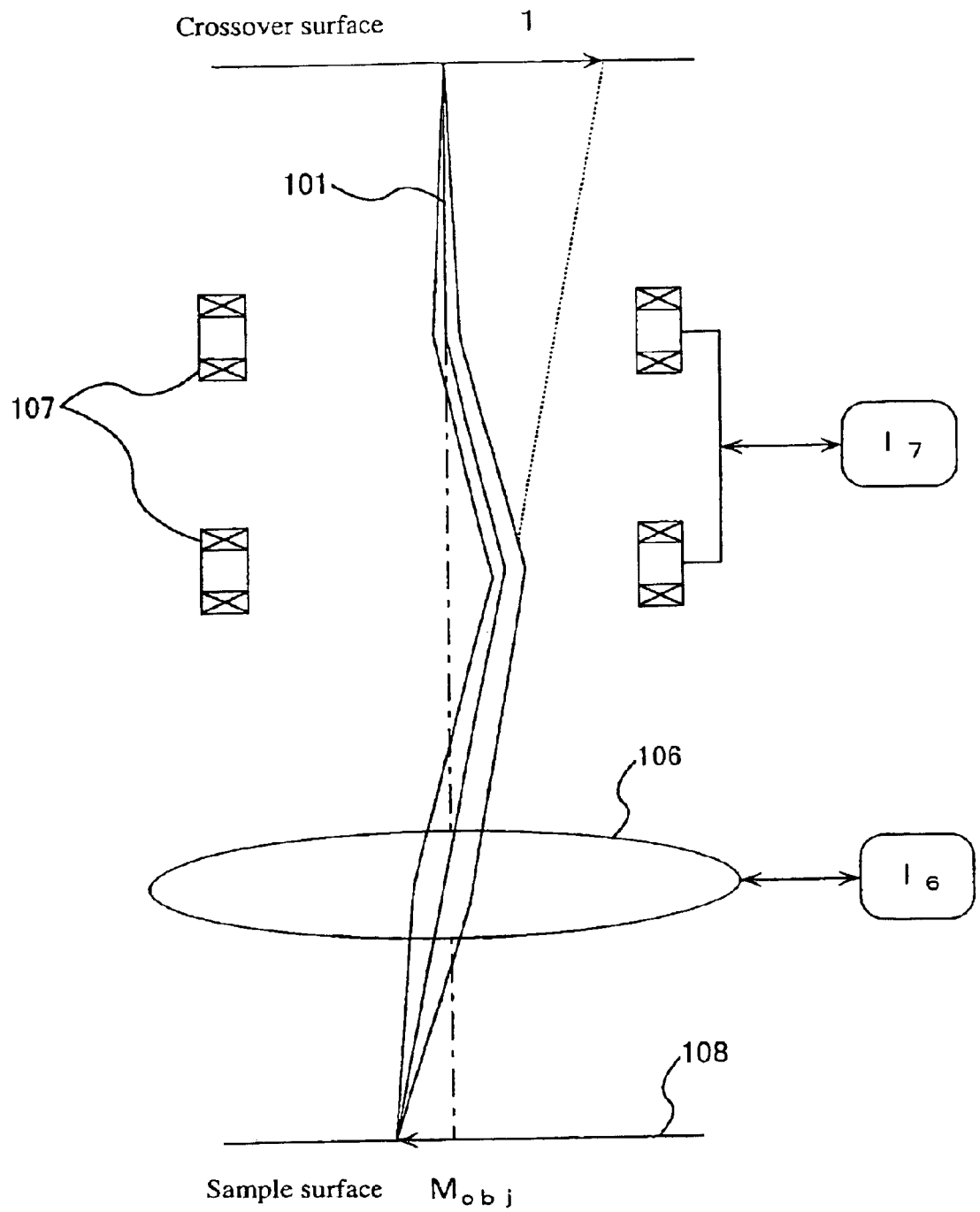
FIG. 9 is a drawing for describing the optical magnification by the objective lens.

FIG. 9 is a concept drawing showing an electronic optical system composed of a scanning deflector, objective lens and sample. This figure shows the relation of the coil current $I_7$ of scanning deflector 107 to the optical magnification $M_{obj}$ of objective lens 106 and observation magnification $M_{SEM}$. The primary electron beam 101 emitted radially from one point on the crossover surface focused on one point on the wafer 108 surface. When the emission point of an imaginary primary electron is separated by an amount 1 from the center axis using the scanning deflector 107, it deviates by $M_{obj}$ on the sample surface. When the conversion coefficient of the scanning deflector 107 and the coil current are respectively set as K and $I_7$, the distance a between two points on the sample can be calculated with the next formula.

$$a = K M_{obj} I_7 \tag{4}$$

Also, when the conversion coefficient of the CRT (display) is L, the distance A between two points on the scanning image on the CRT is shown in the next formula.

$$A = L I_7 \tag{5}$$

Here, considering the case where the optical magnification has shifted from $M_{obj}$ to $M_{obj}'$, the electrical current for scanning the distance between two points a on the sample changes from $I_7$ to $I_7'$, and the distance between two points A on the scanning image of the CRT changes to A'.

$$a = K M_{obj} I_7' \tag{6}$$

$$A' = L I_7' \tag{7}$$

The observation magnification consequently changes from $M_{SEM}$ to $M_{SEM}'$.

$$M_{obj}' = (M_{Obj}/M_{obj}') M_{SEM} \tag{8}$$

Using the following formula allows making correct dimension measurements even if the observation magnification has shifted.

$$a = A'/M_{SEM}' \tag{9}$$

Being able to calculate the optical magnification $M_{obj}$ and $M_{obj}'$ with good accuracy regardless of whether there is an electrostatic charge, allows measuring dimensions with high accuracy.

Figure 10A:
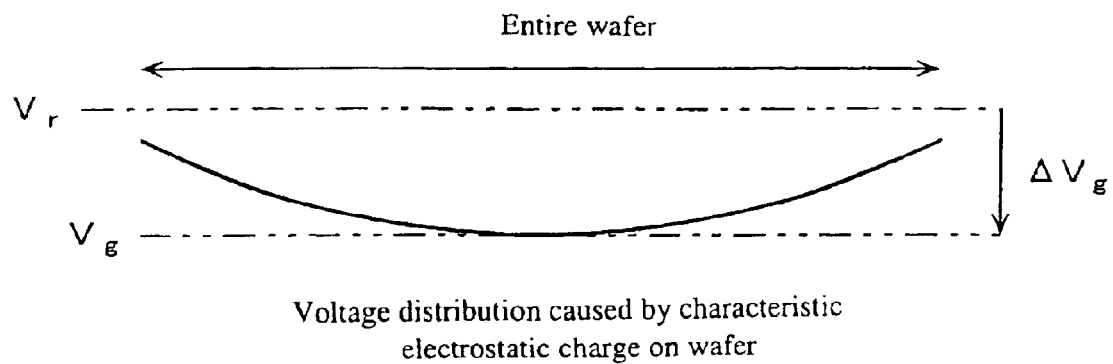
FIGS. 10A, 10B, and 10C are drawings for describing the mechanism causing electrostatic charges on the sample.
Figure 10B:
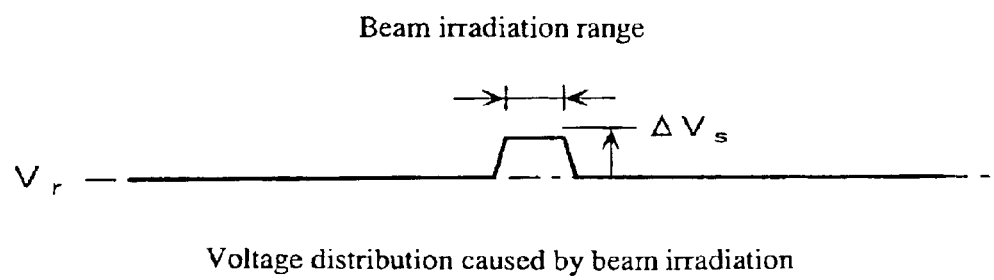
Figure 10C:
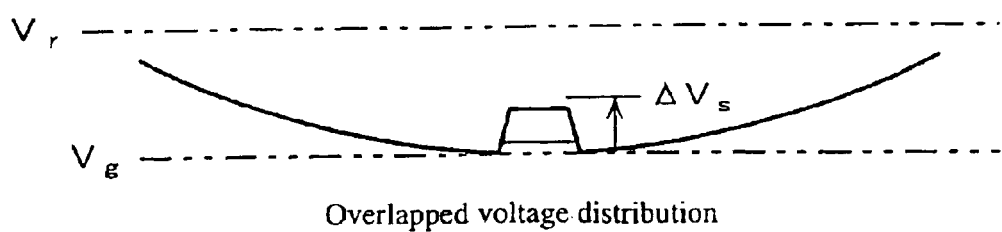

FIG. 10A through 10C are drawings showing the principle of a surface electrostatic charge on the wafer. The retarding voltage $V_r$ is applied to the wafer substrate. FIG. 10A shows the case where the wafer has a characteristic electrostatic charge prior to observation by SEM, because of friction from the spin coater applying the resist coating, or from etching with plasma. The electrostatic voltage in FIG. 10A spans the entire surface of the wafer and is therefore called the wide area electrostatic voltage $\Delta V_g$. The wide area electrostatic voltage in the vicinity of the observation point is $V_g = V_r + \Delta V_g$. The optical magnification $M_{obj}$ at wide area electrostatic voltage $V_g$ is expressed by the following formula (1).

$$M_{obj} = M(V_o, V_g, Z) \tag{10}$$

The function M can be found by electronic optical simulation or by actual measurement. The electrostatic voltage $\Delta V_s$ from the electron beam irradiation on the other hand, is localized as shown in FIG. 10B and is called a localized electrostatic voltage. When both electrostatic charges overlap, the localized voltage in FIG. 10C is $V_s = V_g + \Delta V_s$.

Figure 11:
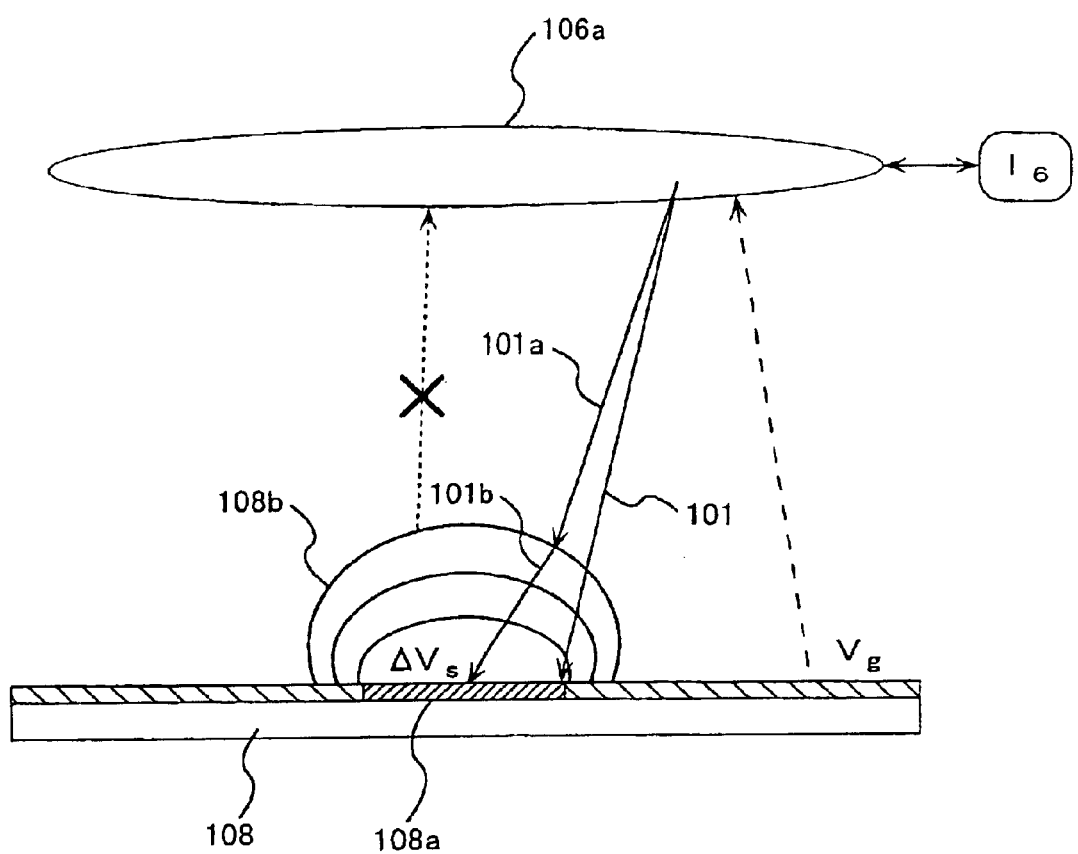
FIG. 11 is a drawing describing the mechanism by which the electrostatic voltage makes the magnification fluctuate.

FIG. 11 is a drawing showing the mechanism by which the wide area electrostatic voltage $V_g$ and localized electrostatic voltage $\Delta V_s$ make the optical magnification $M_{obj}$ of the objective lens change. The wide area electrostatic voltage $V_g$ varies the electrical potential within the objective lens 106a so that an electrostatic lens is formed on the sample and the focus deviates. When this focus is aligned, a marked change occurs in the excitation current $I_6$. This $I_6$ changes and also the energy beamed onto the sample fluctuates so that energy concentrates as in track $1_a$, and the optical magnification $M_{obj}$ fluctuates. Conversely however, $V_g$ can be estimated from the amount of fluctuation in $I_6$.

The electrostatic voltage $\Delta V_s$ from the electron beam irradiation is localized so there is almost no effect on the excitation current $I_6$. Regardless of this, the localized electrostatic voltage $\Delta V_s$ forms a minute static lens 108b so that the primary electrons 101 are concentrated along the track as in 101b, and makes the optical magnification $M_{obj}$ fluctuate greatly. The above description therefore confirms that the wide area electrostatic charge exerts a large effect on the focus and the localized electrostatic charge exerts a large effect on the magnification.

As shown above, the two electrostatic phenomenon have completely different characteristics. The extent of the effect exerted on the focus and magnification by each electrostatic phenomenon is different so that high accuracy correction cannot be achieved even if correcting each of them separately is attempted.

To solve this problem, the wide area electrostatic voltage $\Delta V_g$ and the localized electrostatic voltage $\Delta V_s$, can be isolated and measured, or a means to estimate them can be installed and a means to calculate the correct optical magnification $M_{obj}$ can then be achieved based on this data.

Correcting the deflection intensity of the scanning deflector based on the amount of magnification correction allows accurately displaying a two-dimensional scanning image at the specified observation magnification. Simplifying the magnification correction of the measurement length value itself will prove effective in measurement of dimensions in the semiconductor process.

Figure 12:
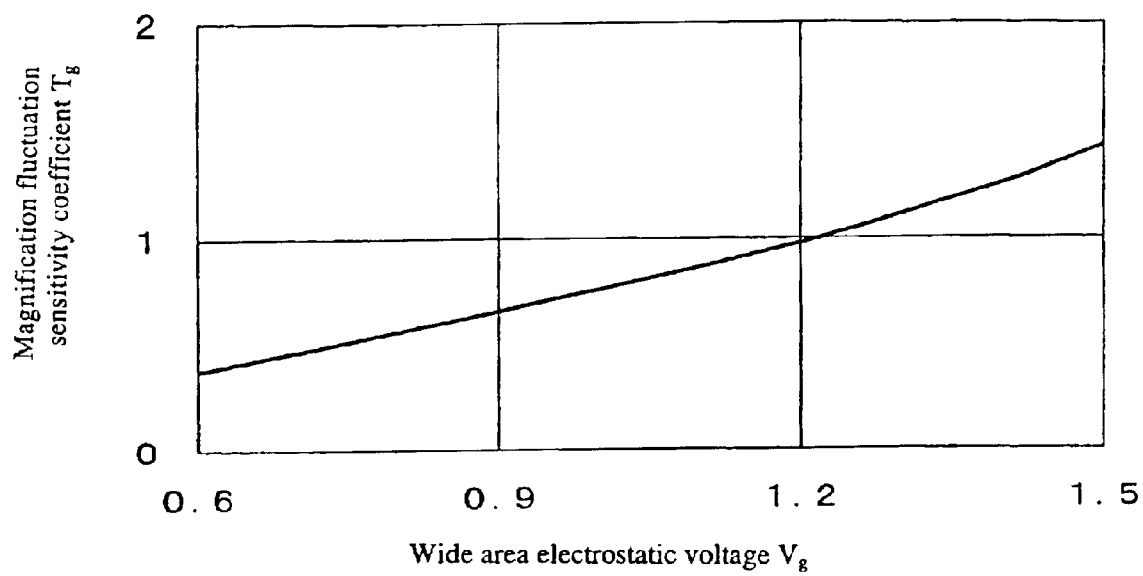
FIG. 12 is a graph showing the relation of the wide area electrostatic voltage and the magnification fluctuation sensitivity coefficient.
Figure 13:
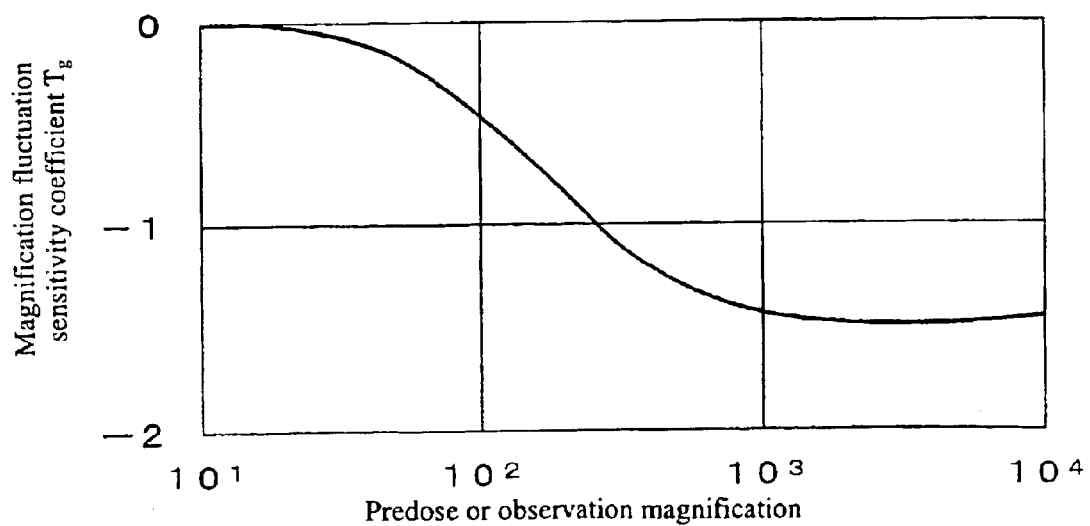
FIG. 13 is a graph showing the relation of the localized electrostatic voltage and the magnification fluctuation sensitivity coefficient.

The effect of the present invention is shown by referring to FIG. 12 and FIG. 13.

FIG. 12 shows the magnification fluctuation sensitivity coefficient $T_g$ when the wide area electrostatic voltage $V_g$ has fluctuated within a range from −0.6 kV to −1.5 kV versus a retarding voltage $V_r = -1.2$ kV. The magnification fluctuation quantity $\Delta M_g = (M_{obj}' - M_{obj})$ can be calculated from $T_g$ and $\Delta V_g$ by the following formula.

$$\Delta M_g / M_{obj} = T_g \Delta V_g \tag{11}$$

Here, the $T_g$ fluctuated due to the wide area electrostatic voltage $V_g$ and observation conditions prior to the electrostatic charge. Therefore each of these observation conditions found by calculation or experiment per the graph of FIG. 8 must be stored. Also, instead of using the formula (11), the magnification $M_{obj}$ or the $M_{obj}'$ may be found directly from the wide area electrostatic voltage $V_g$.

On the other hand, FIG. 13 shows the magnification fluctuation sensitivity coefficient $T_s$ when the beam irradiation area has fluctuated at a retarding voltage $V_r=-1.2$ kV. The magnification fluctuation amount $\Delta M=(M_{obj}'-M_{obj})$ can be calculated from $T_s$ and $\Delta V$, by the next formula.

$$\Delta M_s/M_{obj}=T_s\Delta V_s/V_{acc} \qquad (12)$$

Here, $T_s$ is the fluctuation due to the beam irradiation area size and observation conditions prior to the electrostatic charge. The formula (12) shows a good proportional relationship with the magnification correction $\Delta M_s$ and localized electrostatic voltage $\Delta V_s$. The $T_s$ can be grouped into four sections according to the beam irradiation area (in other words, the beam magnification). A magnification lower than 50 times is regarded as a wide area electrostatic charge. The section from 50 times to 500 times is a transition region from a wide area static charge to a localized static charge. The section from 500 times to 5,000 times is regarded as largely a fixed value. A high magnification from 5,000 times shows a trend for $T_s$ to gradually diminish. Therefore, one side of the irradiation area may preferably be from 10 μm to 300 μm, so as to contain a section where the magnification fluctuation sensitivity coefficient $T_s$ includes a section with a largely fixed value from 500 to 5,000 times. This kind of section allows maintaining the estimated accuracy of the correction value and reduces the number of data that must be stored in advance.

Figure 5:
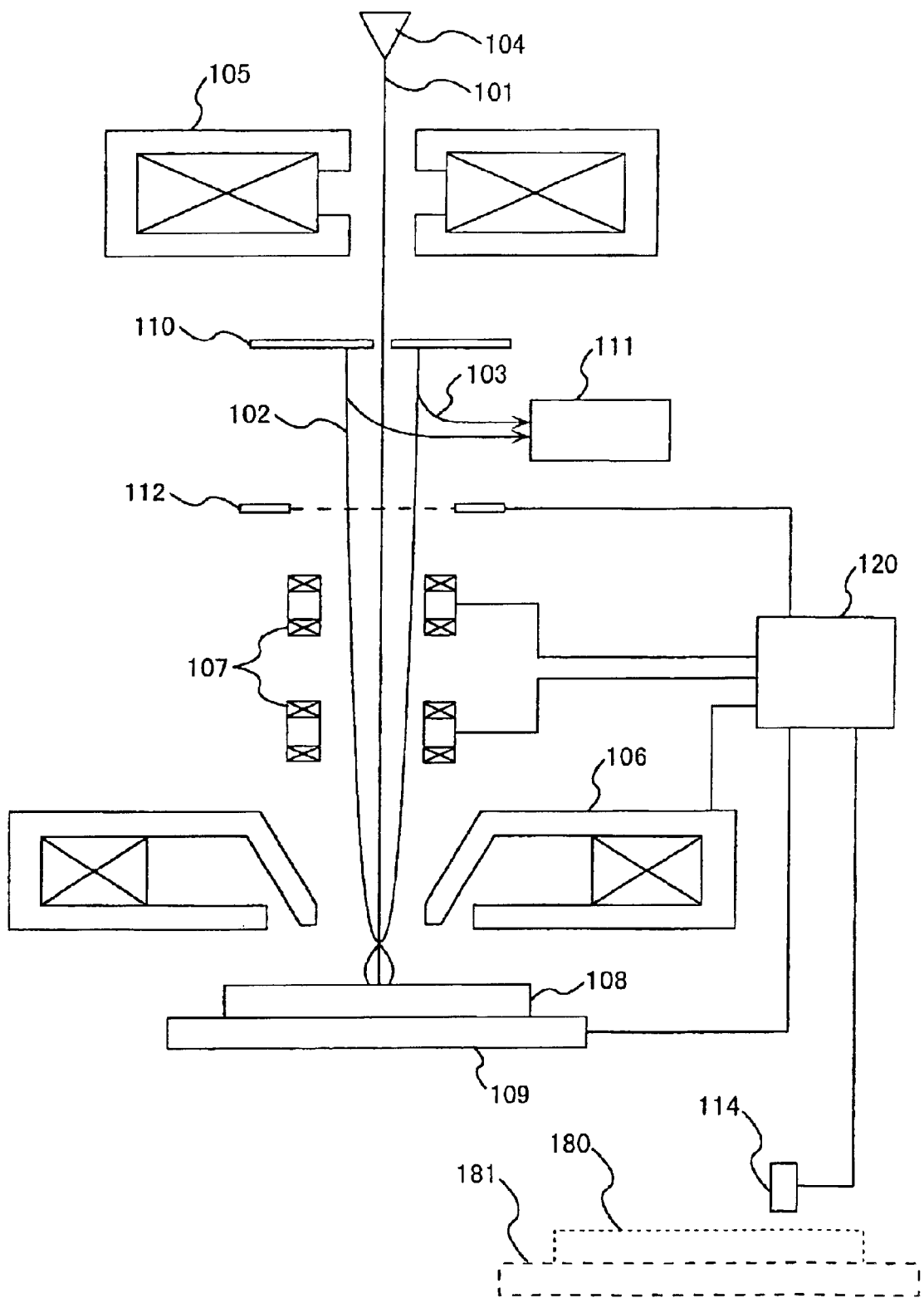
FIG. 5 is a drawing showing the entire structure of the SEM containing a static electrometer and energy filter.

FIG. 5 shows a first working example of the SEM of the present embodiment. The primary electron beam 101 from the cathode (negative electrode) 104 is focused by a condenser lens 105, and two-dimensional scanning of the wafer 108 further performed by the scanning deflector 107. The primary electron beam 101 applies a negative retarding voltage to the wafer 108 via the sample stage 109 so that the beam is decelerated in the decelerating magnetic field between the objective lens 106 and the wafer 108, and the beam on the wafer 108 is narrowed even further by the lens action of objective lens 106.

Secondary electrons 102 are emitted when the primary electron beam 101 irradiates onto the wafer 108. The magnetic field created between the objective lens 106 and the wafer 108 functions as an accelerating magnetic field on the secondary electrons 102 that were generated to pull these secondary electrons 102 into electron beam passage holes of objective lens 106 and these secondary electrons 102 then rise while subject to the lens effect rendered by the magnetic field of objective lens 106. These rising secondary electrons 102 strike the conversion electrode 110 with high energy, to newly generate secondary electrons 103. These secondary electrons 103 are pulled towards the scintillator 111 that was applied with a positive voltage of approximately 10 kV. Light is emitted when the secondary electrons 103 strike the scintillator 111. Though not shown in the drawing, this light is supplied to a photoelectron multiplier tube via a light guide, converted into electrical signals, and after being amplified, the output is used for brightness modulation of the CRT.

The explanation of FIG. 5, described the control processor as being integrated with the scanning electron microscope, or a subsection of the microscope. Needless, to say, the invention is not limited to this example, and a separately installed control processor as described next may be utilized instead of integrated with a scanning electron microscope. In that case, a notification medium for conveying the detection signal detected by the secondary electron detector to the control processor, and conveying the signal from the control processor to the deflector or lens of the scanning electron microscope is required. An input/output terminal is also needed for input or output of the signal conveyed by that notification medium. Further, a control processor to install a program for implementing the following described processing in a storage medium, and comprising a means for supplying the necessary signals to a scanning electron microscope having an image memory, and also executing that program may be used.

The device of the present embodiment contained a static electrometer as described for example in the first embodiment as a measurement means (voltage differential measurement device) for measuring the wide area electrostatic voltage $\Delta V_g$. The wide area electrostatic voltage on the wafer has a concentric circular shape so that the electrical potential distribution of the entire sample can be known by measuring the electrical potential distribution in a linear shape including the center position on the wafer. Therefore the method as described for the first embodiment wherein a static electrometer probe 114 is clamped along the conveyance path of the wafer 108, and the movement of the conveyor arm 181 to measure along a linear shape is applicable. The wide area electrostatic voltage $\Delta V_g$ is expressed as a function of the distance r from the wafer center by utilizing the measurement data, and each the measurement point is moved, a voltage $V_r$ is fed back for the retarding voltage. Also, the voltage that the primary electron beam 101 beams onto the wafer 108 is generally made a fixed voltage value $V_{acc}=V_0+V_g$. Here, $V_0$ is equivalent to the voltage of the cathode 104.

This embodiment also contains a secondary electron energy filter as a measurement means (voltage differential measurement device) for the localized electrostatic voltage $\Delta V_s$. A mesh electrode 112 for example, is installed below the conversion electrode 110. The voltage applied by this mesh electrode 112 is swept using the wide area electrostatic voltage $V_g$ as a reference point, and the signal conversion quantity of the secondary electrons (so-called S curve) measured.

The S curve at the observation point of the actual sample and the S curve measured on a conductive sample surface are compared, and the shift voltage set as the localized electrostatic voltage $\Delta V_s$.

The electrostatic correction controller 120 measures the wide area electrostatic voltage $V_g$, and executes an S curve measurement sequence up to acquiring of a localized electrostatic voltage $\Delta V_s$. The amount of magnification compensation is then calculated based on the excitation current for the objective lens 106 and the $V_g$ and $\Delta V_s$ that were found, and the deflection intensity of the scanning deflector 107 then corrected.

In view of the fact that a localized static charge exerts a large effect on magnification compared to the wide area electrostatic charge, the present embodiment corrects the magnification by subtracting a value equivalent to the wide area electrostatic charge, from an electrostatic charge (localized electrostatic charge) at a specified location. In measuring electrostatic charges merely by using an energy filter, the localized and wide area electrostatic charges (at least an area larger than the scanning area, for example an area larger than an observation area with a magnification of 50 times) are detected in a compounded state. So the present embodiment, by subtracting the electrostatic charge at the electron beam scanning locations measured by static electrometer 114, from the electrostatic charge measured by the energy filter, the localized electrostatic change can be measured based on the actual electron beam without depending on the wide area charge.

This embodiment also allows adjusting the deflection range of the scanning deflector based on the magnification fluctuation quantity $\Delta M_s$ acquired from the above described calculation method. This embodiment also allows correcting the measured length (or end measurement) value.

When adjusting the deflecting range of the scanning deflector and that scanning deflector is the electromagnetic type, the electrical current required for correcting the magnification fluctuation quantity $\Delta M_s$, can be added to or subtracted from the original deflection current to make the adjustment. An accurate measurement length value can also be calculated by multiplying or dividing the magnification fluctuation ratio by the measurement length acquired by a measurement length method used in scanning electron microscopes of the known art and using the result for feedback to the measurement length value. In the present embodiment, the wide area electrostatic charge and localized electrostatic charge were measured while isolated from each other, however methods for adjusting the scanning deflector and methods for correcting the measurement length are not limited to this method.

Figure 6:
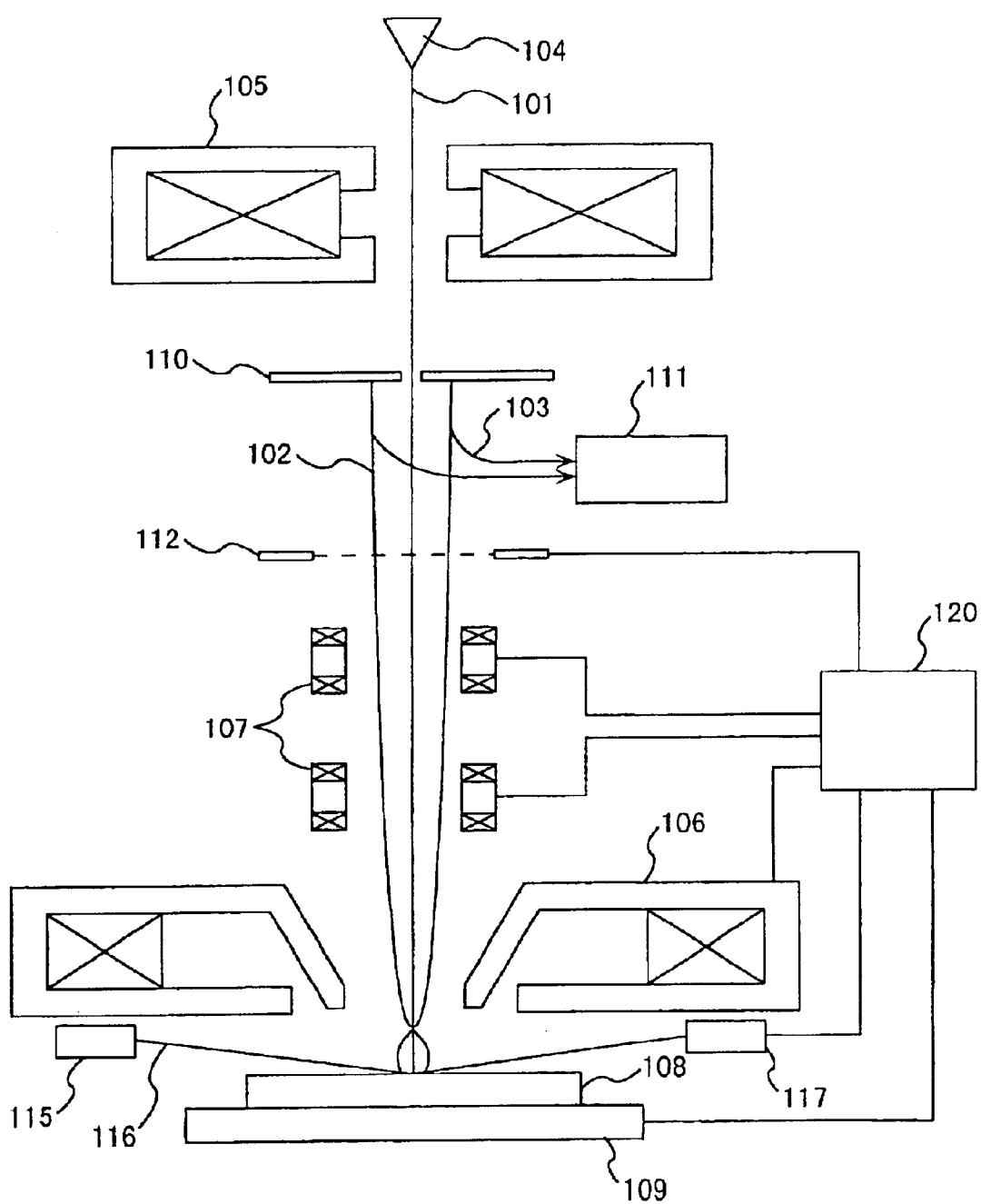
FIG. 6 is a drawing showing the entire structure of the SEM containing an energy filter and sample height measurement means.

FIG. 6 shows a second working example of the present embodiment. In this example, a means to measure the sample height has been added instead of the static electrometer of the previous working example. For example, a laser emission device 115 for detecting the sample height at the point in time that the sample stage 109 has approached the specified measurement point, beams a laser light 116 towards the wafer 108. A so-called Z sensor here is a position sensor 117 receives that reflected light and detects the wafer height from the position that the light was received. The wide area electrostatic voltage $V_g$ is determined from this data on the sample height and excitation current of the objective lens when exactly focused so that if the relation of these three physical quantities are calculated by test or by an electronic optical simulation, then the wide area electrostatic voltage $V_g$ can be estimated without having to directly measure the voltage.

In this embodiment, the electrostatic correction controller 120 executes an S curve measurement sequence until the localized electrostatic voltage $\Delta V_s$ is obtained and sample height measurement with the Z sensor are obtained for estimating the wide area electrostatic voltage $V_g$. Further, the magnification correction quantity is calculated based on the excitation current for the objective lens and by the $V_g$, $\Delta V_s$ found the same way as in the previous working example, and the deflection intensity of the scanning deflector 107 or the acquired length value is corrected.

A different working example of the embodiment is described next. This example is an SEM comprising the static electrometer and the sample height measurement means of the two previous working examples. Since this working example contains these two means, the wide area electrostatic voltage $V_g$ and localized electrostatic voltage $\Delta V_s$ can be measured with even high accuracy and greater stability.

In other words, if the first approximation value $V_{g(1)}$ found from the measurement data of static electrometer probe 114 or by the appropriate expression, and the objective lens excitation current for exact focus estimated and combined with the sample height data from the Z axis sensor, then the exact focusing task (so-called auto-focus) can be completed in a short time. An accurate wide area electrostatic voltage $V_g$ can be calculated from the differential between the excitation current of the autofocus that was found and the excitation current of the objective lens calculated from $V_{g(1)}$. If the $V_g$ is correct, then the $\Delta V_s = \Delta V_s - V_g$ which is the differential versus the localized surface voltage $V_s$ can be accurately calculated, and the magnification correction will have greater accuracy.

Figure 7:
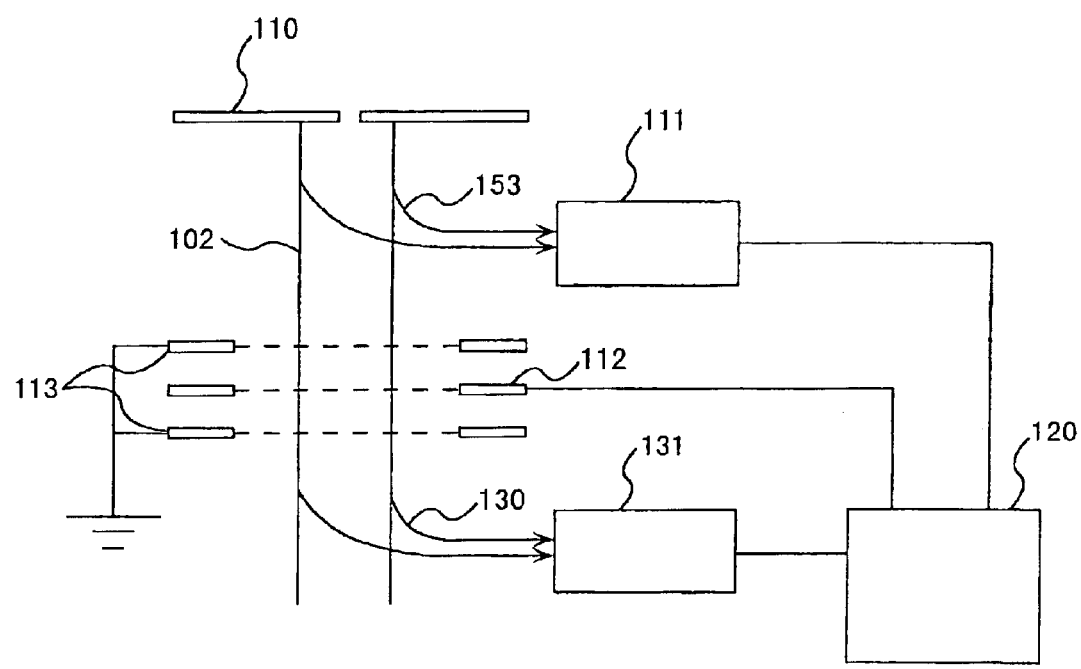
FIG. 7 is a drawing showing the detailed structure of the energy filter.

FIG. 7 is a more detailed view for describing the energy filter for the above embodiment. A mesh electrode 112 is installed enclosed from above and below by the grounded mesh electrode 113 and the secondary electron conversion electrode 110 above it. The mesh electrode 112 voltage is swept using the wide area electrostatic voltage $V_g$ or the first approximation value $V_{g(1)}$ as reset values. The S curve (secondary electron distribution when the voltage applied to the energy filter is changed) is then measured. The grounded mesh electrode 113 prevents the magnetic field of the mesh electrode 112 from unwanted expansion towards the conversion electrode 110, etc. A fixed quantity of secondary electrons 102 strikes the lower mesh electrode 113 without requiring the voltage of the mesh electrode 112, and create a fixed quantity of new secondary electrons 130. These secondary electrons 130 are attracted towards the scintillator 131 to which a positive voltage of approximately 10 kilovolts has been applied. The S curve can be measured with high accuracy by standardizing the current $I_{11}$ from the scintillator 111 with the current $I_{31}$ from scintillator 131. Images can be displayed on the CRT the same as the case with the scintillator 111.

Figure 8:
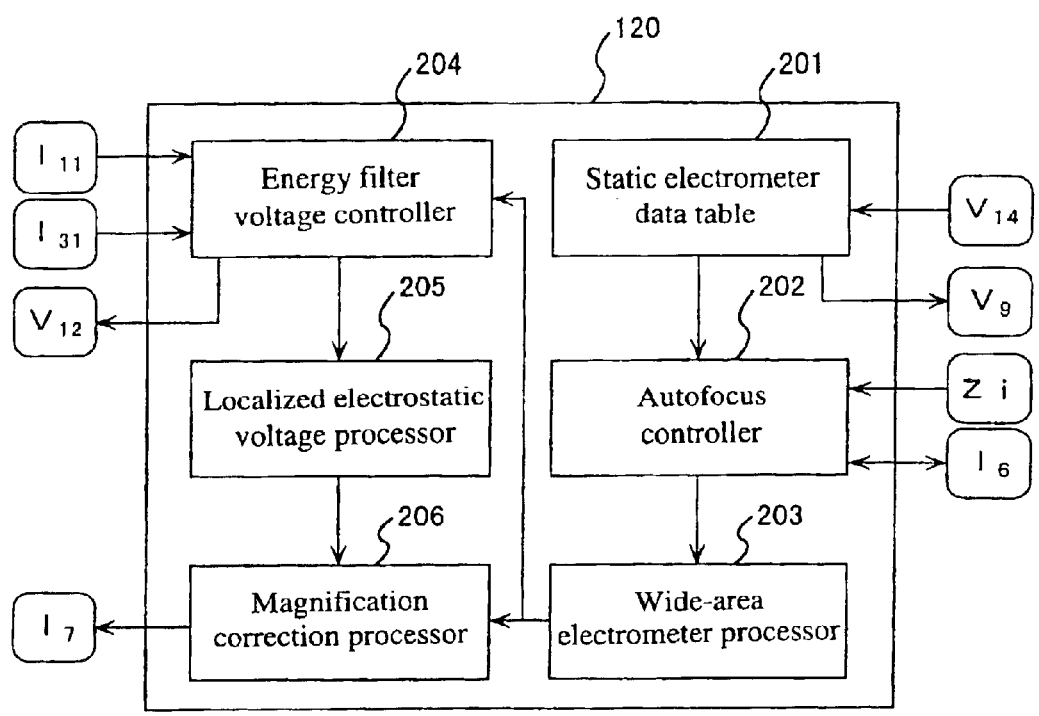
FIG. 8 is a drawing showing the detailed structure of the electrostatic correction controller.

FIG. 8 is a drawing for describing in more detail the electrostatic correction controller 120 for the above three working examples. This electrostatic correction controller 120 is composed of a static electrometer data table 201, an autofocus controller 202, a wide area static electrometer processor 203, an energy filter voltage controller 204 for automatically measuring the S curve, a localized electrostatic voltage processor 205, and a magnification correction processor 206.

First of all, data on the voltage $V_{14}$ for coordinates of the sample measured by the static electrometer or the fitting coefficient are stored in the static electrometer data table 201. The corresponding wide area electrostatic voltage $\Delta V_g$ is measured each time the observation point is moved, and the retarding voltage $V_9$ ($=V_r$) to the sample stage 109 is adjusted so as to satisfy the desired acceleration voltage $V_{acc} = V_0 + \Delta V_g + V_r$. The autofocus controller 202 calculates the excitation current $I_{6(1)}$ for the acceleration voltage $V_{acc}$ set with the sample stage height data $Z_1$ from the Z sensor, and by sweeping the vicinity of this electrical current, search for the excitation current $I_6$ for an exact focus. Next, when there is a differential between $I_{6(1)}$ and $I_6$, the wide area static electrometer processor 203 decides that an error has occurred in $V_{acc}$, and corrects the $\Delta V_g$, to find an accurate wide area electrostatic voltage $V_g$.

The energy filter voltage controller 204 on the other hand, measures the S curve in a non-charged state, and stores it in the localized electrostatic voltage processor 205. In the S curve measurement sequence, the applied voltage $V_{12}$ of mesh electrode 112 is swept using the wide area electrostatic voltage $V_g$ or its estimated value $V_{g(1)}$, as a reference just as described above, and changes in the electrical current $I_{11}$ of the secondary electrons are measured. The electrical current $I_{31}$ from the scintillator 31 can also be standardized here. The data to be stored may be data that was already processed such as the S curve itself, or filter voltages in excess of a threshold, filter voltages with a maximum S curve slope. The S curve varies somewhat depending on the sample material so data may also be recorded for each sample so that calculation accuracy can be enhanced from then onwards. The localized electrostatic voltage processor 205 selects the S curve to be used as the reference, and calculates the localized electrostatic voltage $\Delta V_s$ from the amount of voltage shift. Finally, the magnification correction processor 206 uses the respective formulas (1) and (2) from the wide area electrostatic voltage $V_g$ and localized electrostatic voltage $\Delta V_s$ to calculate the magnification correction amounts $\Delta M_g$ and $\Delta M_s$. By then correcting the electrical current $I_7$ of the scanning deflector with the inverse of the total magnification $M+\Delta M_g+\Delta M_s$, an image can always be observed at the desired magnification regardless of the electrostatic voltage.

An effective method for boosting the processing speed when automatically processing large numbers of wafers on a semiconductor production line, is to reduce the number of S curve measurements by the energy filter. With an identical circuit pattern, and identical material, the localized electrostatic voltage $\Delta V_s$ will be the same (for each wafer) so a $\Delta V_s$ that was already measured can be utilized. In some cases, one S curve measurement for each wafer will also suffice. When a new S curve is measured, it is automatically added to the database of localized electrostatic voltage processor 205.

In the present embodiment, the fluctuation in the magnification rate can be calculated with high accuracy for dimension measurement and image observation of the insulation material of the sample. Also, fluctuations in the measurement length value can be corrected by setting a fixed desired magnification rate or magnification change. Dimensions can in this way be controlled with high accuracy in the currently ultra-miniaturized semiconductor fabrication process.

A supplementary result also obtained is that image quality is stabilized since the energy of the primary electron beam irradiation onto the sample can be controlled to a high degree of accuracy. Further, by monitoring the localized electrostatic voltage $\Delta V_s$, the destruction of the dielectric (insulation) by excessively large electrostatic charges can be prevented, and an electrostatic voltage or index thereof can be obtained for bottom surface observation via large aspect ratio contact holes.

(Third Embodiment)

The localized electrostatic voltage $\Delta V_s$ varies the optical magnification $M_{obj}$ of the objective lens as described using FIG. 11. The electrostatic voltage $\Delta V_s$ is localized due to electron beam irradiation so there is almost no effect on the excitation current $I_6$. Regardless of this, the localized electrostatic voltage $\Delta V_s$ forms a minute electrostatic lens 108b. This lens causes the track 101a of the primary electron beam to be deflected by the global (wide area) electrostatic charge so as to concentrate onto the track 101b and make the optical magnification $M_{obj}$ greatly fluctuate as described in the previous embodiment.

Yet another method is described next for making accurate tests and measurements that are otherwise difficult due to different, overlapping electrostatic phenomenon.

The present embodiment proposes a method for correcting the magnification fluctuation using the localized electrostatic voltage $\Delta V_s$ and calculating the correct optical magnification $M_{obj}$.

The magnification fluctuation brought about by the localized electrostatic charge is dependent on the localized electrostatic voltage $\Delta V_s$. The localized electrostatic voltage $\Delta V_s$ is dependent on the electron beam irradiation magnification (in the present embodiment, this is hereafter called the predose magnification, mainly in order to describe electron beam irradiation prior to using electron beam for testing and measurement) $M_{pre}$ and magnetic field near the sample surface and the type of sample.

Figure 14:
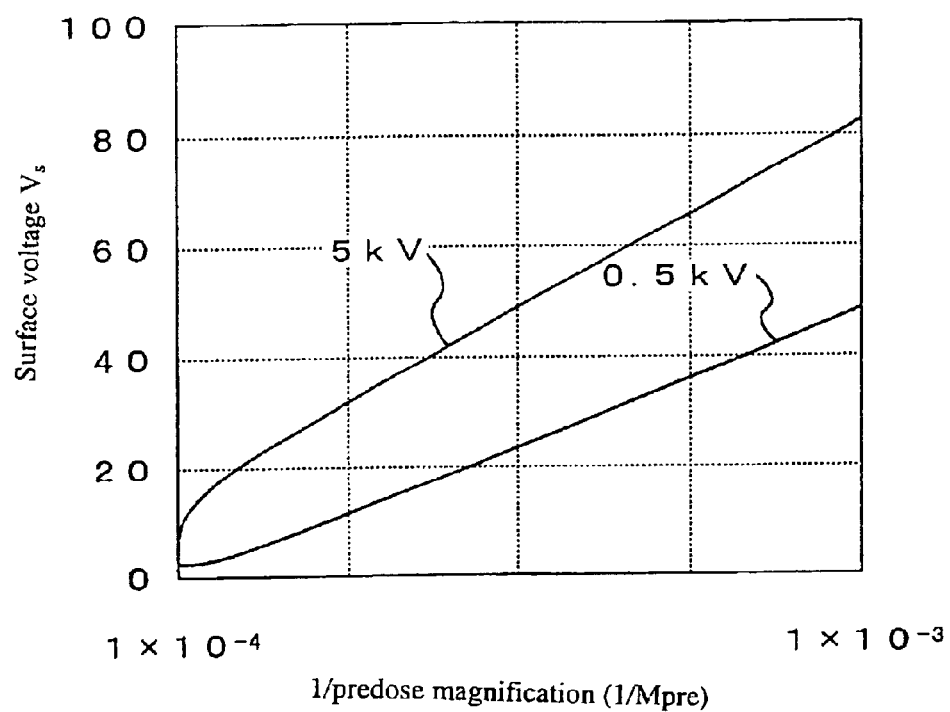
FIG. 14 is a graph showing the relation of the localized electrostatic voltage and the irradiation area of the irradiation electron beam.

FIG. 14 shows the localized electrostatic voltage $\Delta V_s$, when the predose magnification $M_{pre}$ was varied at boosting voltages of 0.5 kV and 5 kV. The boosting referred to here is a method for installing a cylindrical electrode to be applied with a positive voltage within the objective lens so that the electron beam within the objective lens can at least reach a high acceleration to pass through the objective lens. FIG. 14 shows the results when the surface electrical potential was measured after varying the predose magnification while a voltage of 0.5 kV was applied to the cylindrical electrode, and while 5 kV was applied. This boosting technology is disclosed in detail for example in JP-A No. 171791/1997 (U.S. Pat. No. 5,872,358).

When the predose magnification and the sample surface electrical field are used as parameters for varying the localized electrostatic voltage $\Delta V_s$, then the localized electrostatic voltage $\Delta V_s$ can be calculated in the following fitting function from the boosting voltage $V_b$, retarding voltage $V_r$, fitting coefficients $A_1$ and $a_1$, and predose magnification $M_{pre}$ parameters.

$$\Delta V_s = A_1(V_b-V_r)/M_{pre}+a_1 \quad (13)$$

Also, the magnification fluctuation quantity $\Delta M/M_{obj}$ can be calculated from $\Delta V_s$ using the magnification sensitivity coefficient $T_s$.

$$\Delta M/M_{obj}=T_s\Delta V_s \quad (14)$$

Figure 15:
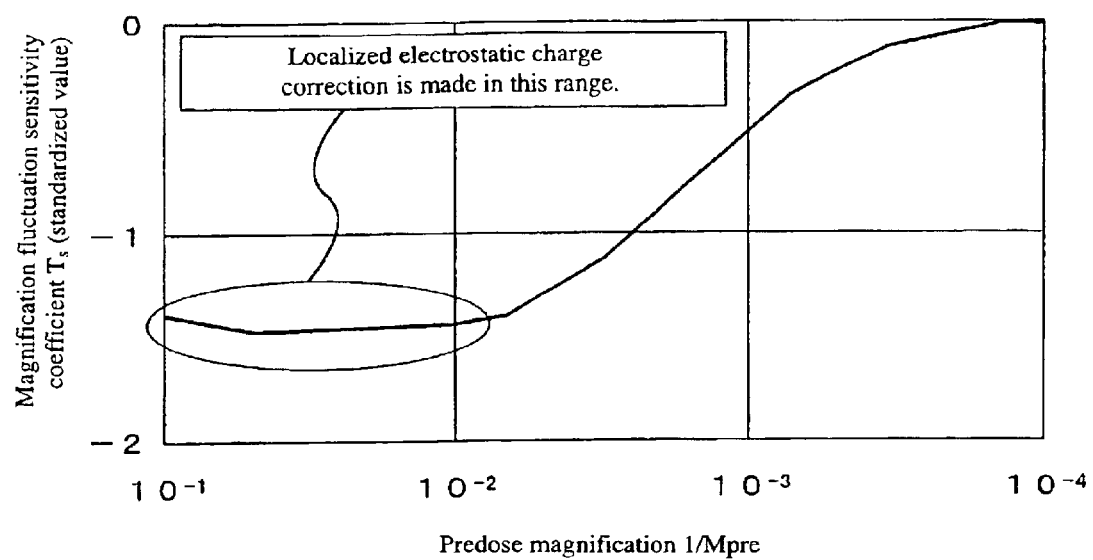
FIG. 15 is a graph showing the relation of the magnification fluctuation sensitivity coefficient and the magnification of the irradiation electron beam.

FIG. 15 shows the magnification fluctuation sensitivity coefficient $T_s$, when the beam irradiation area ($\propto 1$/predose magnification=$1/M_{pre}$) was varied at a retarding voltage of $V_r=-1.2$ kV. $T_s$ can be grouped into four sections according to the beam irradiation area. A section with a low magnification rate below 50 times is regarded as a global electrostatic charge.

A section from 50 times up to 500 times is a transition region from the global electrostatic charge to a localized electrostatic charge. A section from 500 times up to 5,000 times is regarded as largely fixed. A section with a high magnification from 5,000 times upward has a tendency for the $T_s$ to diminish. Therefore, if the magnification fluctuation sensitivity coefficient $T_s$ of the irradiation area is set as an irradiation area (1 side is from 10 μm to 300 μm) equivalent to a magnification of 500 times to 5,000 times regarded as a fixed area, then the number of pre-stored data can be reduced while still maintaining the estimated correction value accuracy.

When the true value and actual measured value of the pattern dimensions are respectively set as L, $L_{ex}$, the magnification fluctuation quantity $B=\Delta M/M_{obj}$, can be calculated from the following formula.

$$L/L_{ex}=1+B \quad (15)$$

When estimating the true measured length using formula (13), formula (14), formula (15), the unknown coefficients are $A_1$ and $a_1$. Therefore, if the $(V_b-V_r)$ proportional to the electrical field of the sample surface or the predose magnification $M_{pre}$, is changed and results from measuring two or more points are utilized, then the true measurement length L value can be estimated.

This method has the advantage that when observing an unknown insulation sample, the true measurement length can be estimated by changing the charge location of the sample surface or the predose magnification $M_{pre}$, and measuring two or more different localized electrostatic voltage $\Delta V_s$. Also, when using this method, instead of a fitting coefficient having a predose magnification and surface charge location as electrostatic variable parameters to vary the localized electrostatic voltage $\Delta V_s$, as shown in formula (13); the same results can be obtained with another fitting coefficient having the energy of the input beam, irradiation time and electrons within the sample and the degree of hole movement as the charge variable parameters.

By storing fitting coefficients $a_1$ and $A_1$ in the memory, true dimension values can be estimated by using the measurement length value for one predose magnification and surface electrical field. The fitting coefficient $a_1$ used in formula (13) on the other hand, is not dominated by the predose magnification and surface electrical field. Therefore, by substituting in the formula (13), formula (14) and formula (15) for irregularities in the $a_1$ utilized when correcting the measurement length of the same type of sample, the reliability of the adjusted parameters used to make the correction can be evaluated by means of the deviation in measurement length.

Figure 16:
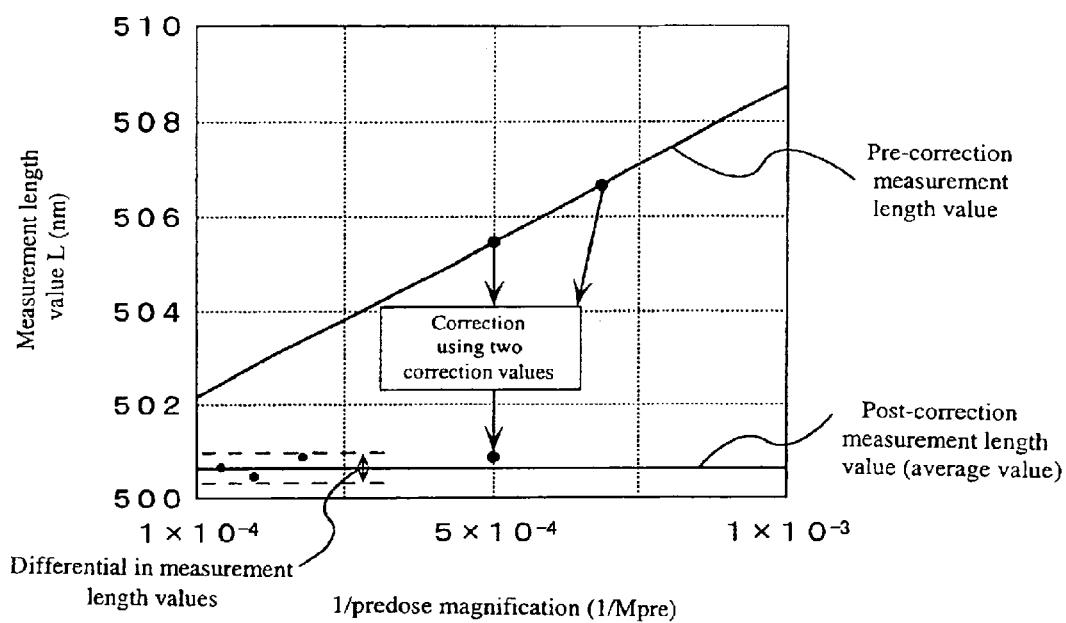
FIG. 16 is a graph showing the relation of the predose magnification, actual measurement length value and estimated measurement length value.

FIG. 16 is a graph showing the relation of the measurement length value before correction to the measurement length value after correction versus predose magnification. By storing the magnification fluctuation amount B for each predose magnification calculated from the true dimension values and measurement length before correction, the true dimension value can be estimated from the measurement length value of one observation condition.

When performing the predose, a high contrast image can be obtained by utilizing the optimal acceleration voltage shown in JP-A No. 200579/2000 and higher accuracy measurement results can be obtained.

A function for estimating the true dimension values (per the means of the first working example of the embodiment) by utilizing the measurement length value of multiple points where the charge variable parameters for varying the localized electrostatic voltage were changed, is described next in an example using electrostatic correction controller 120 of FIG. 5 and FIG. 6.

Figure 17:
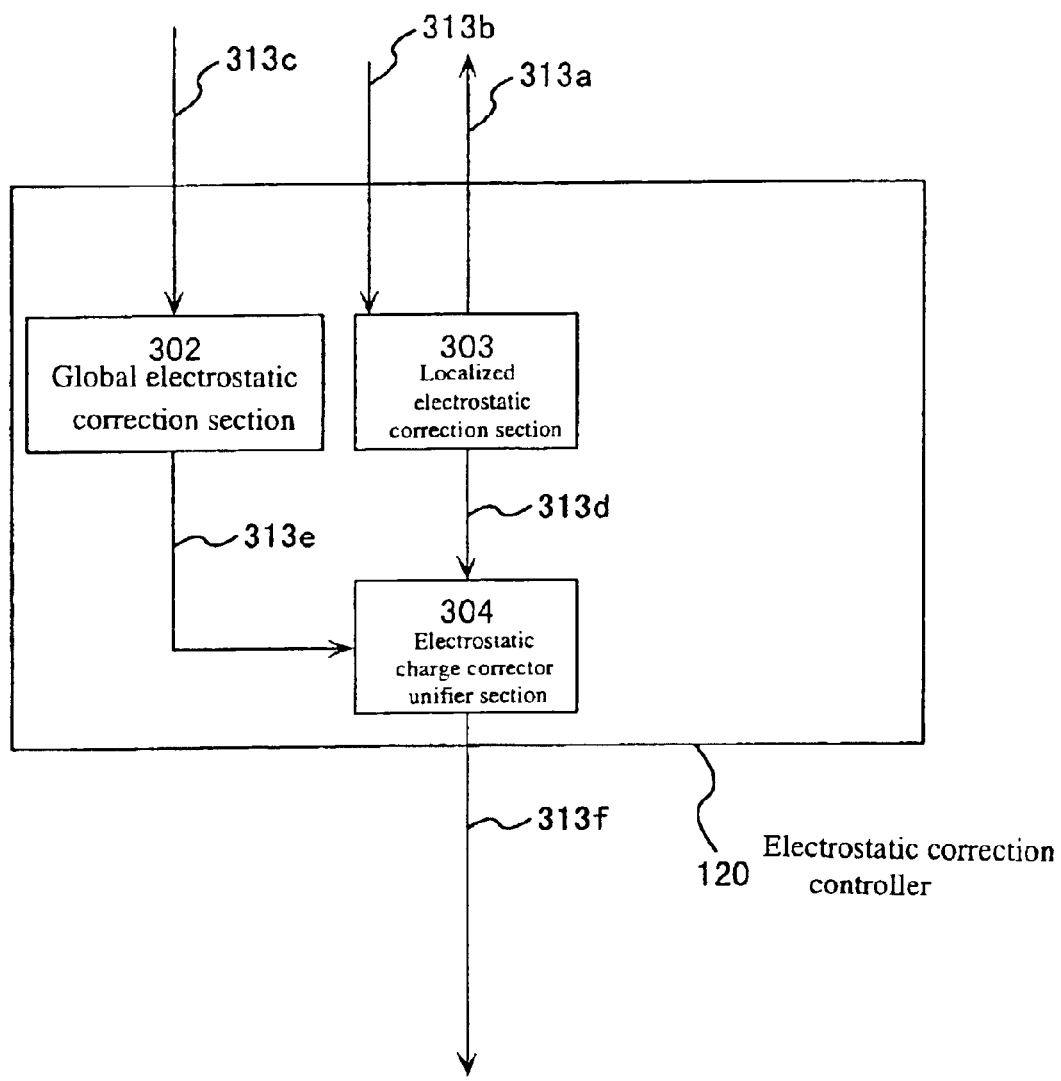
FIG. 17 is a block diagram of the localized electrostatic charge correction section.

FIG. 17 is a block diagram of the electrostatic correction controller 120. The electrostatic correction controller 120 is comprised largely of a global electrostatic correction section 302 and localized electrostatic correction section 303. The localized electrostatic correction section 303 sets the measurement conditions (charge variable parameters, acceleration voltage, and primary electron beam irradiation time during predose) via 313*a*.

The measurement length measured per the conditions that were set is input from an input device (not shown in drawing) via 313*b* to the localized electrostatic correction section 303. A magnification fluctuation amount B for correcting the localized electrostatic charge based on the measurement conditions that were set and the measurement length that was input, are input via 313*d* to the electrostatic charge corrector unifier section 304. Also, the magnification fluctuation amount calculated in the global electrostatic correction section 302 is also input to the electrostatic charge corrector unifier section 304 via 313*e*.

The dimensions whose varied measurement length was corrected by the effect of the global electrostatic charge and localized electrostatic charge, was output from the magnification fluctuation amount derived in the respective correction section of global electrostatic correction section 302 and localized electrostatic correction section 303 that were input from the electrostatic charge corrector unifier section 304.

Figure 18:
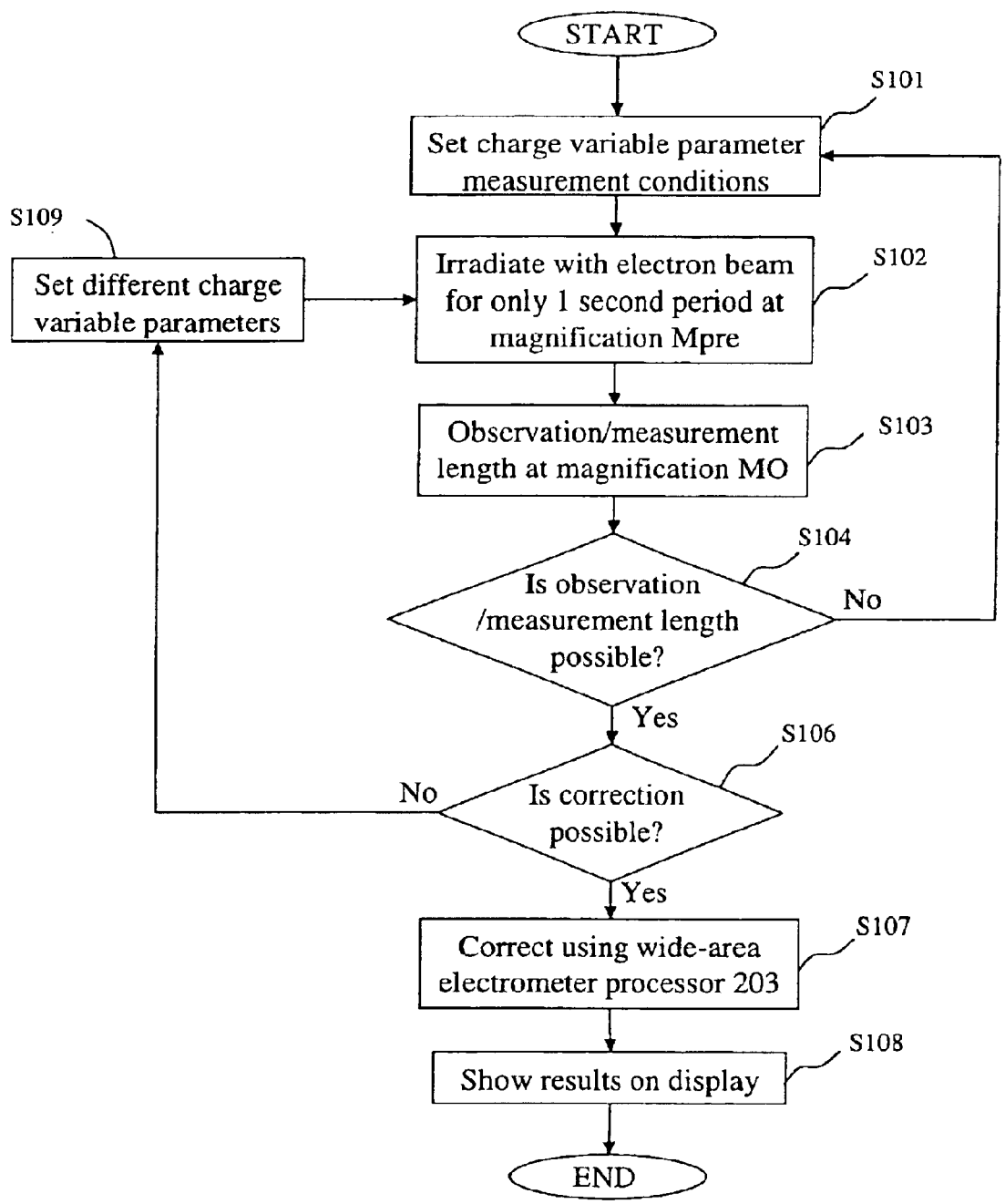
FIG. 18 is a flow chart showing the procedure for correcting the localized electrostatic voltage based on measuring the electrostatic charge at two or more points.

FIG. 18 is a flow chart showing the process for correcting the measurement length value. First of all, the charge variable parameters and measurement conditions are set in step s101. Next, in step s102, the electron beam irradiates the sample to create an electrostatic charge according to the conditions set in step s101. In step s103, the measurement length value $L_{ex}$ is acquired by measurement under the charge variable parameters established in step s101 or step s109. In step s104, a decision is made whether the measurement length $L_{ex}$ acquired in step s103 has sufficient accuracy. When decided the measurement length was not sufficiently accurate, the observation condition settings of step s101 are corrected.

In step s106, a decision is made whether data has been collected enough times for correction in step s107. If there is not enough data, then different charge variable parameters are set in step s109 and measurement length again measured. In step s107, the measurement length value is corrected by using the measurement length value measured in step s105 and the charge variable parameters established in step s102 and step s109. The measurement length value corrected in step s108 is output to the monitor.

By using the localized electrostatic correction in the present embodiment, the true dimension value can be estimated with high accuracy by making two or more measurements with different localized electrostatic voltages, even on samples of materials and shapes that have had no preliminary measurement. Further, the measurement speed is improved because no preliminary measurement with an energy filter is required for each magnification.

Figure 19A:
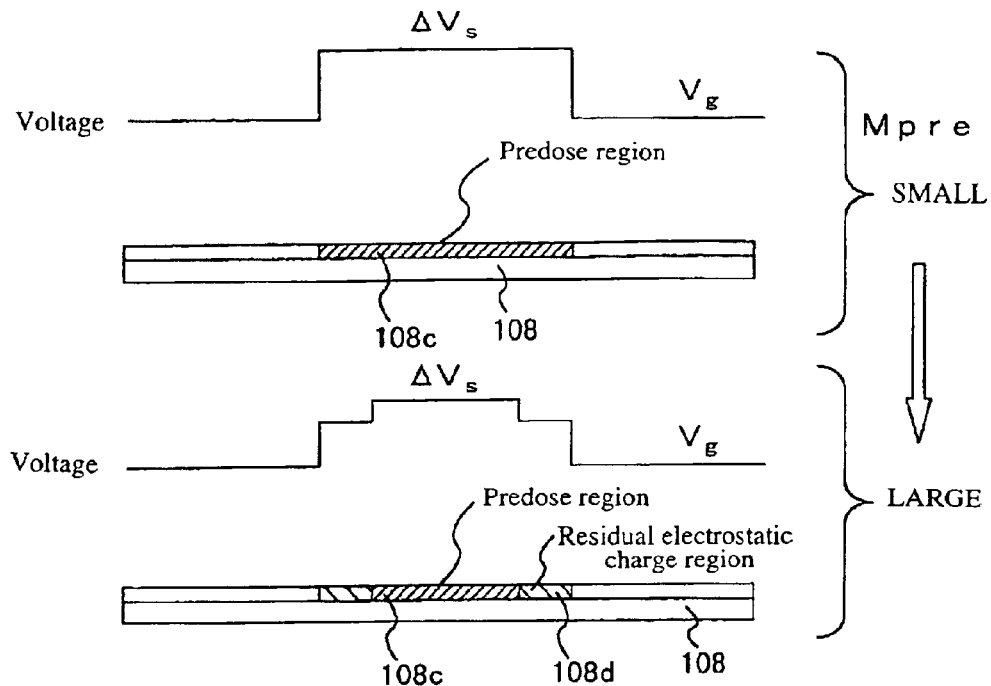
FIGS. 19A and 19B are drawings showing the electrostatic charge state during predose magnification.
Figure 19B:
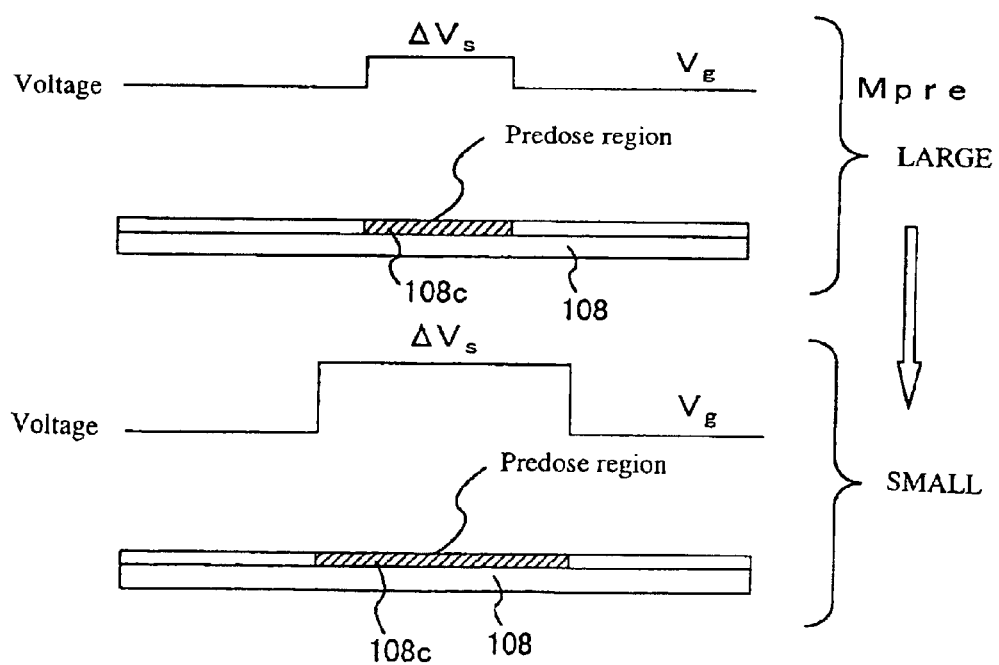

FIG. 19A to FIG. 19B show drawings of sample electrostatic charges when the predose magnification was changed and the sample given an electrostatic charge. During length measurement at respective magnifications using two or more different predose magnifications, a stable localized electrostatic charge can be quickly formed by using the following procedure.

The sample 108 hold two types of electrostatic charges; a global (wide area) electrostatic charge $V_g$ spanning the entire surface and a localized electrostatic voltage $\Delta V_s$ created by the electron irradiation. In FIG. 19A, a residual electrostatic region 108*d* can be formed when the predose magnification is raised during observation after that predose magnification was observed in a small state. The localizes static charge correction is badly effected unless sufficient time is taken for the charge on the residual electrostatic region to sufficiently weaken. However if the predose magnification is lowered after observation of a large predose magnification as shown in FIG. 19B, then there is no residual electrostatic region, so measurement can start immediately after the predose ends since no weakening time is required. Using the above procedure allows rapid observation with good accuracy in an electrostatic region.

Figure 20:
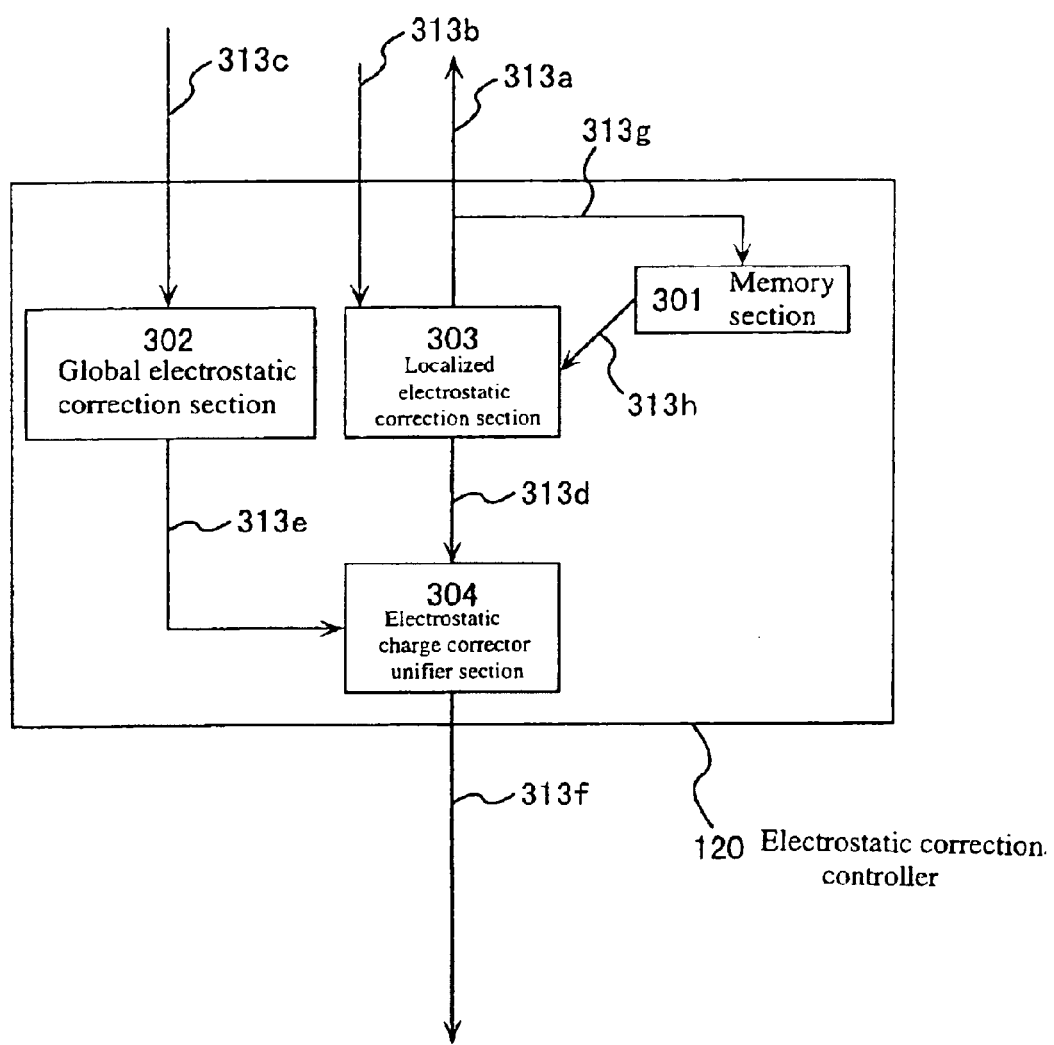
FIG. 20 is a block diagram of another localized electrostatic charge correction section.

The second working example of the embodiment of the present invention is described next while referring to FIG. 20 and FIG. 21. In this embodiment, the memory section 301 in the electrostatic correction controller 120, contains a database of fitting constants for functions expressing the magnification fluctuation amount B or localized electrostatic voltage $\Delta V_s$. Measurement conditions (charge variable parameters, acceleration voltage, and primary electron beam time during predose) from localized electrostatic correction section 303 via 313*a* are set here.

The measurement length value measured under the preset conditions, is input via 313*b* to the localized electrostatic correction section 303. The magnification fluctuation amount B or the charge variable parameters are input to the memory section 301 via 313g. The $\Delta V_s$ matching the charge variable parameters input in memory section 301 and fitting coefficient linked to the variable change parameters or the magnification fluctuation amount B are input to the localized electrostatic correction section 303 via 313h. After correction of the measurement length value calculated using the data that was input, the measurement length value is output via 313d.

Figure 21:
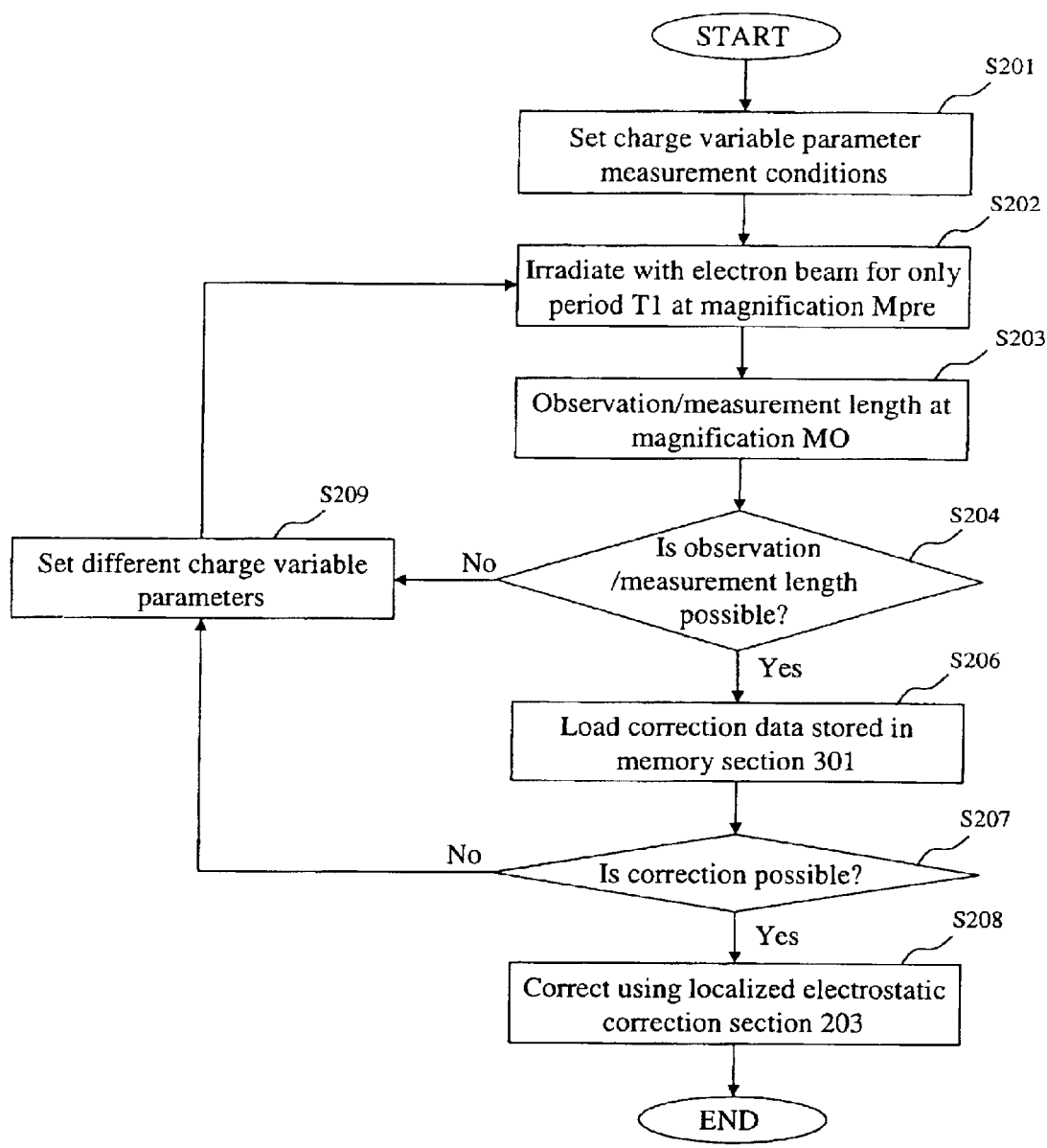
FIG. 21 is a flow chart showing the procedure for correcting the localized electrostatic charge when correction data is available in the memory section.

FIG. 21 is a flow chart showing the measurement procedures when storing the correction data. The charge variable parameters and measurement conditions are set in step s201. Next, in step s202, the electron beam irradiates the sample to create an electrostatic charge according to the conditions set in step s201. In step s203, the measurement length value $L_{ex}$ is acquired by measurement under the charge variable parameters established in step s201 or step s209. In step s204, a decision is made whether the measurement length $L_{ex}$ acquired in step s203 has sufficient accuracy. When decided the measurement length was not sufficiently accurate, the observation condition settings of step s209 are corrected.

In step s206, fitting coefficients for showing the magnification fluctuation amount B or the $V_s$, derived previously under the same charge variable parameters as correction data are loaded from the memory section 301. In step S207, a decision is made if correction is possible or not from the measurement length value $L_{ex}$ that was acquired and from the charge variable parameters established in step s201 or step s208. When decided that correction is impossible, the observation conditions are reset in step s209.

In step s208, the measurement length value $L_{ex}$ measured in step s205 is input to the localized electrostatic correction section 303. The measurement length value is at the same time obtained after correction by the localized electrostatic correction section 303, using this data.

Performing localized electrostatic correction using this embodiment, allows shortening the time required for measurement length since this localized electrostatic correction can be performed from a measurement length value measured under one charge variable parameter for a sample measured once and having at least the same pattern and same condition. If the optimal predose conditions such as shown in JP-A No. 200579/2000 in step s201 are set, then stable measurements can be made with high accuracy.

In the third working example of the present embodiment, in order to increase the reliability of the corrected measurement length, the memory section 301 contains a database holding fitting coefficients for fitting coefficients for magnification fluctuation amount B or $V_s$, and measurement conditions of the same type sample previously measured.

In this embodiment by utilizing a memory section 301 containing the above described database, the measurement length value can be quantitatively evaluated by means of the differential in accuracy after localized electrostatic correction. A threshold value is set from the differential of this measurement length value. If a measurement length exceeding this threshold setting is measured, then this measurement is judged as abnormal and a decision is made whether the cause of the abnormal measurement is effects from impurities on the sample surface or an abnormal electrostatic charge, etc.

The procedure used in this embodiment is shown next. First of all, the procedure for constructing the database is shown. The localized electrostatic voltage $\Delta V_s$ of the sample is changed, and adjusted coefficients for localized electrostatic voltage at multiple points are derived from measurement length values measured between the same points. The fitting coefficients for the fitting coefficients of localized electrostatic voltage $\Delta V_s$, for the same type sample from between different two points are found in the same way.

Among the multiple fitting coefficients found by repeating this process, the irregularities of fitting coefficient $a_1$ not dependent on the charge variable parameters are extracted. Irregularities of fitting coefficient $a_1$ and irregularities of the fitting coefficient $a_1$ corrected with the length measurement differential are stored in the memory section 301.

Figure 22A:
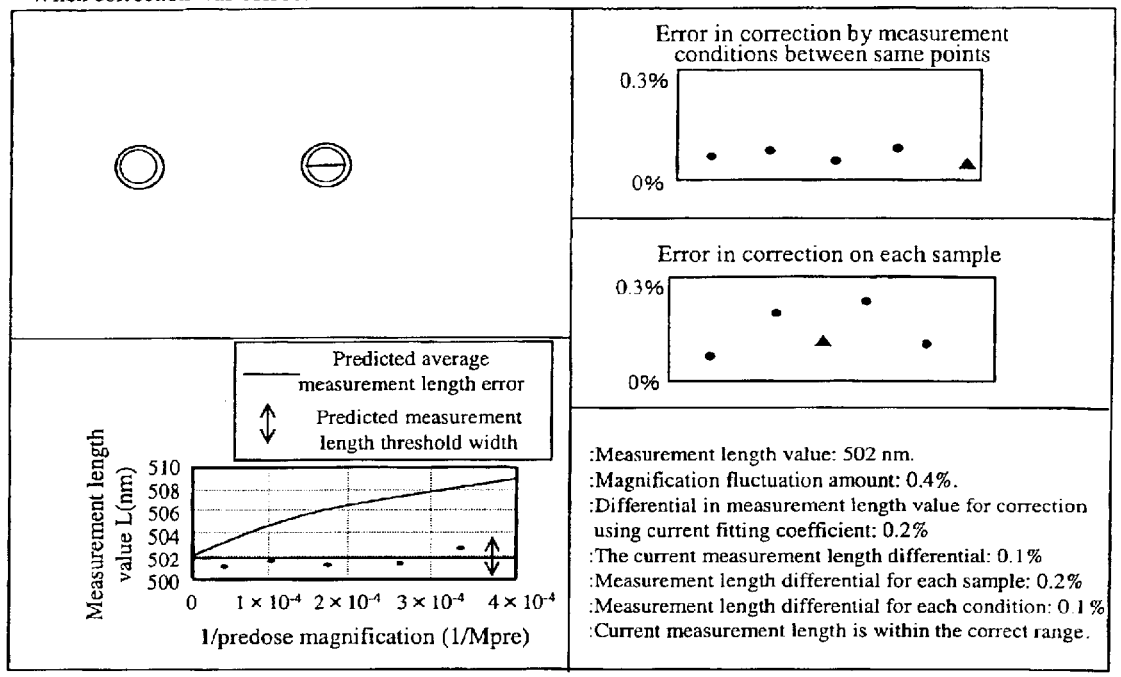
FIG. 22A and FIG. 22B are drawings showing the error check screen for estimated measurement length from localized electrostatic correction.
Figure 22B:
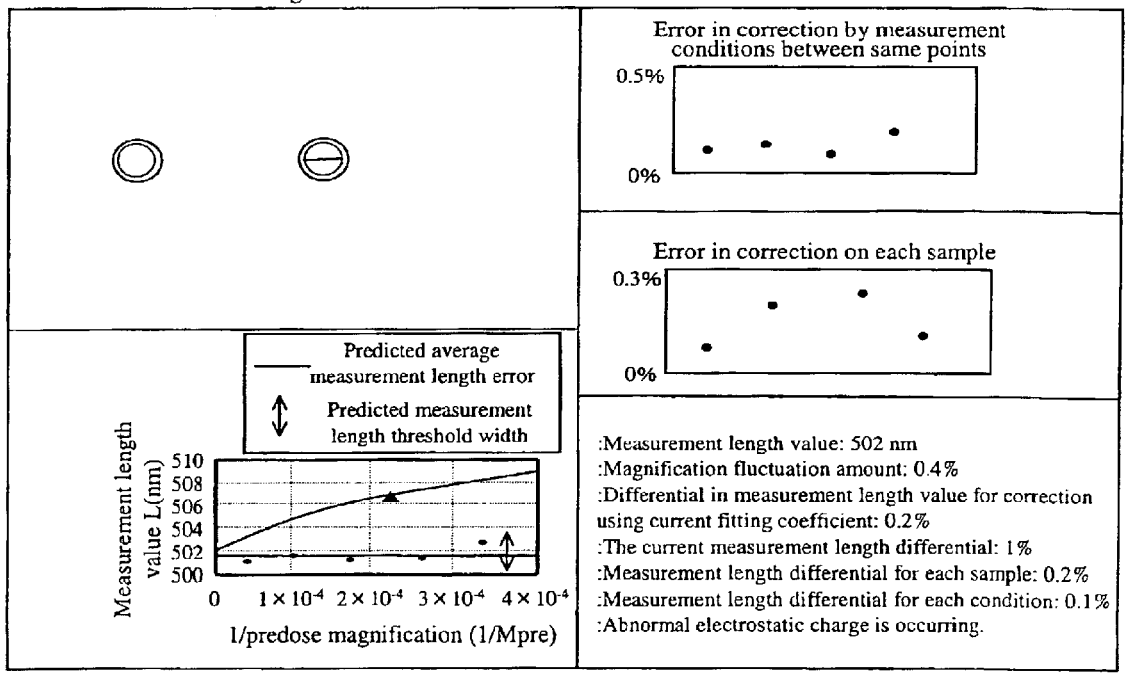

Next, the procedure for deciding if there is an abnormal electrostatic charge is shown by using the database that was formed. When the measurement length value derived from the changing the charge variable parameter and measuring the measurement length (each time the sample is replaced or a length measurement made) exceeds the threshold value found from the differential with the stored length measurement value in the memory section 103, then a screen display as shown in FIG. 22A and FIG. 22B appears and the user is notified of an abnormal electrostatic charge.

When the fitting coefficient $a_1$ currently utilized in this correction is within the thresholds found from the irregularities of the previously measured fitting coefficient a,stored in memory section 301, this shows there is no abnormality and the localized electrostatic charge is judged to be normal.

When the fitting coefficient a, currently utilized in this correction exceeds the thresholds found from the irregularities of the previously measured fitting coefficient a, stored in the memory section 301, this shows that an abnormal electrostatic charge has occurred. Utilizing this embodiment therefore allows knowing whether a localized electrostatic charge is abnormal or not so that the length measurement can be found with a high degree of reliability.

Figure 23:
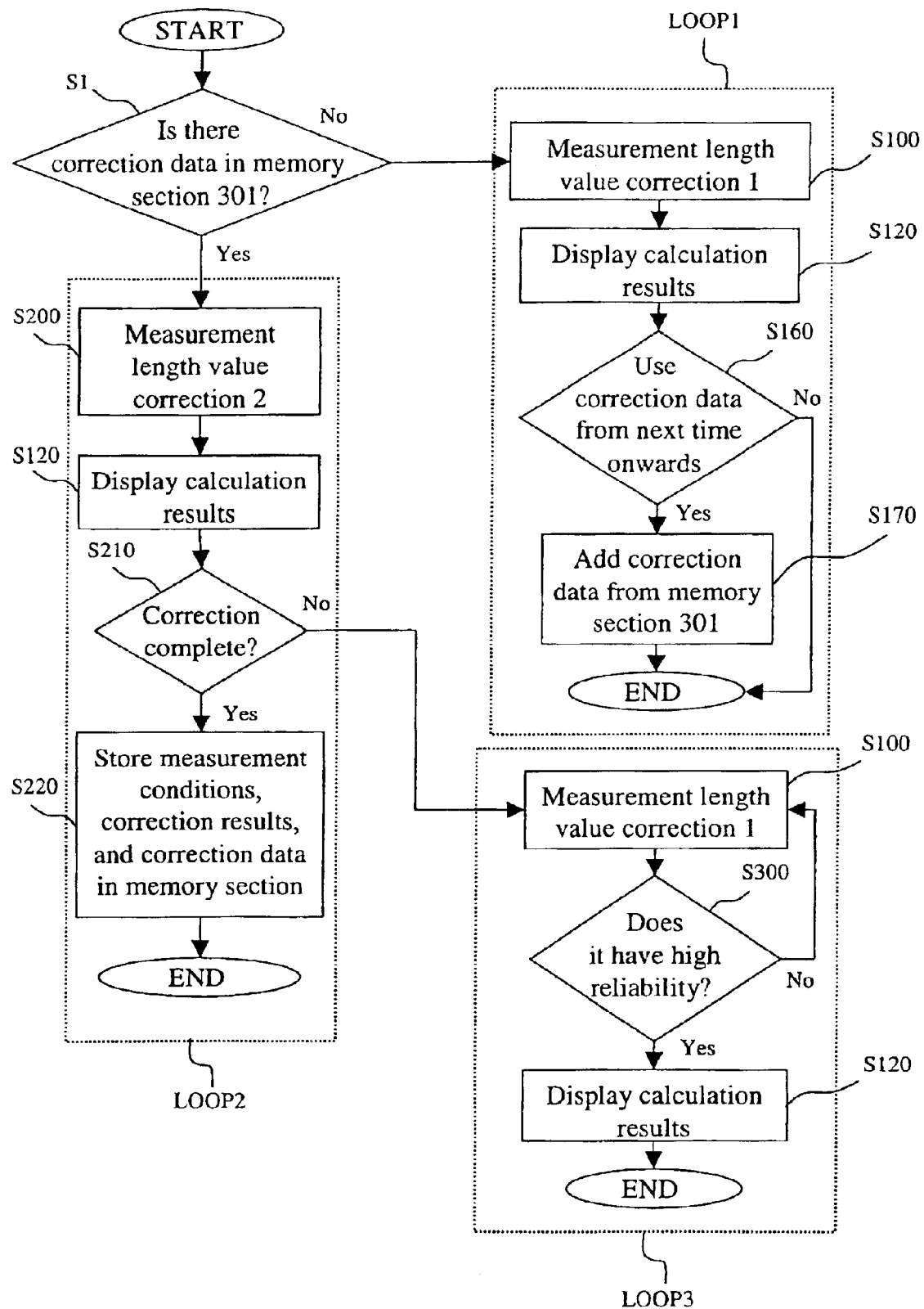
FIG. 23 is a flow chart showing the procedure for a composite of multiple embodiments.

The fourth working example of the present embodiment combines the functions of all the above embodiments. A flow chart of the process of the present embodiment is shown in FIG. 23. In step s1, a decision is made whether or not there is correction data in the memory section 301 for the current observation sample. When the correction data needed for the current measurement length does not exist (no correction data), the process in the flow of loop 1 in step s100 shown in the first working example is performed to derive the post-correction measurement length value L.

In step s120 and step s160 the correction results are shown on a screen, and whether or not the currently used correction data will be used from the next time onwards is decided. If to be used from the next time onwards, then the correction data is stored in the memory section 301 in step s170. In step s1 when there is correction data, the flow of loop 2 starts and the processing shown in the second working example is performed to derive a post-correction measurement length L. The correction results displayed on the screen area shown in FIG. 22A and FIG. 22B.

When the evaluation shown in the third working example is made and an abnormal electrostatic charge is detected in step s210, a warning is displayed and loop 3 starts. By repeatedly performing the procedure shown in the first working example multiple times, a fitting coefficient $a_1$ is output under multiple conditions. In step s300, an fitting function is made using an average value for irregularities in the multiple fitting coefficients found in step s100.

The reliability of the currently formed fitting function is evaluated from the differential in measurement lengths from irregularities in multiple fitting coefficient $a_1$. If decided that the fitting function is not reliable, then the process returns once again to step s100. When decided in step s300 that a fitting function was obtained that is sufficiently reliable versus abnormal electrostatic charges, the calculation results for the measurement length differential and post-correction measurement length values using the fitting function currently made in step s120 are displayed on the screen.

By performing localized electrostatic correction using the present embodiment, during length measurement of the same patterns cut into the same insulation piece sample, the measurement length process can be performed at higher speeds and with more uniform accuracy.

Figure 24:
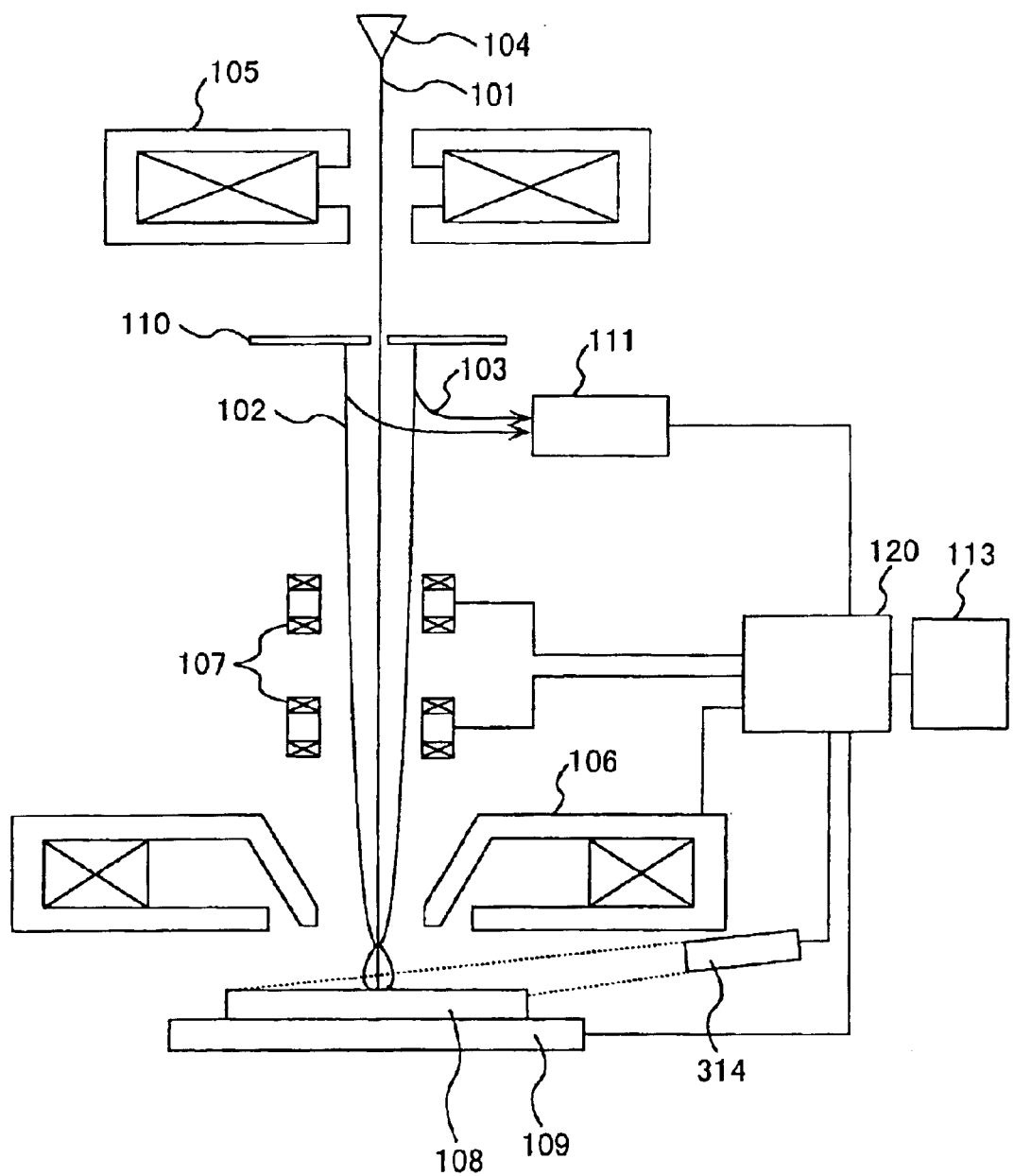
FIG. 24 is an overall concept drawing of an SEM containing an ultraviolet beam device.

The fifth working example of the present embodiment described here utilizes a scanning electron microscope comprising an ultraviolet beam device 314 for minimizing effects on the previously measured electrostatic charge. FIG. 24 is a block diagram showing the scanning electron microscope comprising an ultraviolet beam device 314. The reference number 113 in the drawing denotes the input device for entering the measurement conditions. By irradiating the sample with an ultraviolet beam from the ultraviolet beam device 314 for each observation, the electrostatic charge accumulated on the sample from the previous measurement can be reset so that stable measurement of dimensions can be performed.

The embodiments can therefore calculate the amount of fluctuation in observation magnification with high accuracy for making dimension measurements and image observation of the insulation sample. The dimensions in the currently ultra-miniaturized semiconductor fabrication process can in this way be controlled in a short time with high accuracy.

What is claimed is:

1. A method for measuring the electrostatic charge on a sample, characterized by comprising the steps of:

measuring the electrical potential distribution in a specified direction on the surface of said sample by using a static electrometer when said sample is loaded into the sample chamber of a scanning charged particle beam device; and estimating the electrical potential distribution along a two-dimensional direction on the surface of said sample, based on the change in electrical potential measured in the specified direction.

2. A method for measuring the electrostatic charge on a sample according to claim 1, characterized in that:

in the step for estimating the electrical potential distribution two-dimensionally on the surface of said sample, the electrical potential distribution function on said sample is calculated from the change in electrical potential in said specified direction, and from the conveyance speed of said sample.

3. A method for measuring the electrostatic charge on a sample according to claim 1, characterized in that the electrical potential of the irradiation point of said scanning charged particle beam is estimated based on said estimated electrical potential distribution in a two-dimensional direction on said sample surface.

4. A charged particle beam irradiation method characterized by comprising the steps of:

measuring the electrical potential distribution in a specified direction on the surface of said sample by using a static electrometer;

estimating the electrical potential distribution along a two-dimensional direction on the surface of said sample, based on said electrical potential distribution measured in said specified direction; and adjusting the focus conditions of said charge particle beam based on the electrical potential estimated at the specified points, when irradiating said scanning charged electron beam onto said specified points on said sample.

5. A method for measuring the electrostatic charge on a sample, characterized by comprising the steps of:

measuring the electrical potential at multiple points on the surface of said sample using multiple static electrometers installed at positions separated from said sample conveyance path, when said sample is loaded into the sample chamber of a scanning charged particle device; and estimating the electrical potential distribution along the surface of said sample, based on multiple measured voltages measured.

6. A charged particle beam irradiation method characterized by comprising the steps of:

measuring the electrical potential at each point on the surface of said sample by using multiple static electrometers;

estimating the electrical potential distribution along a two-dimensional direction on the surface of said sample, based on the multiple measured electrical potentials; and adjusting the focus conditions of said charge particle beam based on the voltage estimated at said specified points, when irradiating said scanning charge electron beam onto said specified points on said sample.

7. A scanning charged particle device with a loader mechanism for loading a sample into a sample chamber, and measuring a sample based on secondary charged particles emitted due to irradiation by a charged particle beam onto said sample loaded by said loader mechanism, characterized in that said scanning charged particle beam device further contains a static electrometer installed along the track for conveying said sample material loaded by said loader mechanism for measuring the electrical potential on said sample, and further contains a control device for calculating the electrical potential distribution along the surface of said sample, based on the electrical potential distribution of said sample measured by said static electrometer.

8. A scanning charged particle beam device according to claim 7, characterized in that said electrical potential measurement probe of said static electrometer is installed along said transport path of said sample.

9. A scanning charged particle beam device according to claim 8, characterized in that said electrical potential measurement probe is installed outside said sample chamber.

10. A scanning charged particle beam device according to claim 8, characterized in that said electrical potential measurement probe and said loader mechanism are installed in order to maintain a fixed distance from each other during conveyance of said sample.

11. A scanning charged particle beam device according to claim 7, characterized in that said loader mechanism conveys a holder for gripping said sample, and said holder is constructed to reach electrical ground during measurement of electrical potential by said static electrometer.

12. A scanning charged particle beam device according to claim 7, wherein said control device comprises a function to adjust the focus of said charged particle beam, and adjust the focus according to said charged particle beam irradiation position on said sample, based on said electrical potential measurement.

13. A scanning charged particle device according to claim 12, comprising a power supply to apply a negative voltage to said sample, characterized in that said control device forms an arithmetic formula based on a function of the distance from the center of said sample based on the electrical potential of said sample measured by said static electrometer, and possesses a function to control said power to apply a voltage to said sample according to the coordinates of said sample based on said arithmetic formula.

14. A scanning charged particle device according to claim 13, characterized in that the function for the distance from the center of said sample is an even function of a quadratic or higher.

15. A scanning charged particle device with a loader mechanism for loading a sample into a sample chamber, and measuring a sample based on secondary charged particles emitted due to irradiation by a charged particle beam onto said sample loaded by said loader mechanism, characterized in that said scanning charged particle device further contains a static electrometer for measuring the electrical potential on said sample during conveyance of said sample loaded by said loader mechanism, and further contains a control device for changing the focusing conditions of said focusing means for focusing said charged particle beam, based on the electrical potential distribution of said sample measured by said static electrometer.

16. A charged particle beam irradiation method for scanning the charged particle beam onto said sample, and detecting charged particles emitted from a scanning region of said sample, characterized by comprising the steps of:

measuring the electrical potential distribution on said sample surface;

measuring the localized electrical potential on said scanning region of said charged particle beam; and subtracting the electrical potential of a section containing said scanning locations among said measured electrical potential distribution, from the electrical potential of said scanning locations, and measuring the localized electrostatic charge of said scanning locations.

17. A charged particle beam irradiation method according to claim 16, characterized in that the deflection intensity of a deflector for deflecting said charged particle beam is adjusted based on said localized electrostatic charge.

18. A charged particle beam irradiation method according to claim 16, characterized by comprising:

a step to measure the pattern dimensions on said sample based on detection of charged particles emitted from the scanning region on said sample; and a step to correct said measured pattern dimension values based on said localized electrostatic charge values.

19. A scanning charged particle beam device comprising:

a charged particle beam supply;

a scanning deflector to scan the charged particle beam emitted from said charged particle beam power supply; and a detector for detecting the charged particles emitted from said sample material based on irradiation of charged particle beam onto a sample, characterized in that with said scanning charged particle beam device further comprises:

an electrical potential measuring device for measuring the surface electrical potential of charged particle beam scanning locations on said sample;

an electrical potential distribution measurement device for measuring the electrical potential distribution of a region wider than said scanning locations; and a control section for subtracting the electrical potential of said scanning location measured with said electrical potential distribution measurement device, from said surface electrical potential measured with said electrical potential measurement device.

20. A scanning charged particle beam device according to claim 19, characterized in that the deflection range of said scanning deflector is adjusted to correct fluctuations in magnification occurring due to a voltage, based on said subtracted voltage.

21. A scanning charged particle beam device according to claim 20, characterized in that said control device possesses a correction algorithm forming a relation proportional to the amount of correction for fluctuations in said magnification with said subtracted electrical potential.

22. A scanning charged particle beam device according to claim 19, characterized in that said control device measures the pattern dimensions on said sample based on charged particle detected by said detector, and corrects the fluctuations in said pattern dimension values occurring due to said electrical potential, based on said subtracted electrical potential.

23. A scanning charged particle beam device according to claim 22, characterized in that said control device possesses a correction algorithm forming a relation proportional to the amount of correction for fluctuations in said pattern dimensions with said subtracted electrical potential.

24. A scanning charged particle beam device according to claim 19, characterized in that the irradiation surface area of said scanned charged particles is a rectangular shape with one side from 10 to 300 micrometers.

25. A scanning charged particle beam device according to claim 19, characterized in that said control device contains a table expressing the relation of the localized electrostatic voltage to the irradiation energy of said charged particle, irradiation surface area, and localized shape and material of said sample, or a means for storing an empirical formula; and searches said table for a localized electrostatic voltage most matching the measurement conditions, or estimates said measurement conditions from said empirical formula.

26. A scanning charged particle beam device comprising: a charged particle beam power supply; a scanning deflector for scanning with a charged particle beam emitted from said charged particle beam power supply; a detector for detecting charged particles emitted from said sample based on said charged particles irradiating said sample; and a device for measuring the height of said sample, characterized in that said scanning charged particle beam device further comprises:

an electrical potential measurement device for measuring the surface electrical potential of charged particle beam scanning locations on said sample; and a control device to measure and calculate the electrical potential of an area wider than the scanning locations of said scanning charged particle beam from the induction current of said objective lens and said measured height of said sample.

27. A sample dimension measurement method for detecting charged particle beam emitted from the sample based on scanning said sample with charged particles, and measuring the pattern dimensions on said sample based on said detected charge particles, characterized by comprising the steps of:

irradiating with said charged particle beam under at least two different irradiating conditions with electrostatic charges caused by charged particle beam scanning; and forming a fitting function for expressing changes in said electrostatic voltages due to changes in said irradiation conditions, in order to correct said pattern dimensions based on said fitting function.

28. A sample dimension measurement method according to claim 27, characterized in that said two different irradiation conditions change the irradiation magnification of said charged particle beam.

29. A sample dimension measurement method according to claim 27, characterized in that said two different irradiation conditions change the electrical field of the irradiation area of said charged particle beam.

30. A scanning charged particle beam device comprising: a charged particle beam power supply; a scanning deflector for scanning with a charged particle beam emitted from said charged particle beam supply; a detector for detecting charged particle beam emitted from said sample based on said charged particles irradiating said sample; and a control device for measuring pattern dimensions on said material based on the output from said detector, characterized in that said control device contains a memory device for storing a fitting function for showing changes in the electrostatic voltage on said sample versus changes in irradiation conditions of said charged particle beam, and corrects said pattern dimensions based on said stored fitting function.

31. A scanning charged particle beam device according to claim 30, characterized in that when measuring said pattern dimensions, said control device performs calculations using said fitting function, based on irradiation conditions of said charged particle beam.

32. A scanning charged particle beam device according to claim 30, characterized in that said fitting function is proportional to the electrical field on said sample, and inversely proportional to said magnification.

* * * * *